United States Patent
Sagel et al.

(10) Patent No.: US 9,566,225 B2
(45) Date of Patent: Feb. 14, 2017

(54) PRODUCTS AND METHODS FOR DISCLOSING CONDITIONS IN THE ORAL CAVITY

(75) Inventors: Paul Albert Sagel, Maineville, OH (US); Cloyd Dixon, Jr., Florence, KY (US); Ivo Kunath, Kronberg (DE); Martin Haas, Eschborn (DE); Jens Uwe Stoerkel, Frankfurt am Main (DE); Armin Andreas Tschol, Reutte (AT); Lucy Abigail Zimmermann, Kronberg (DE); Steffi Raehse, Munich (DE)

(73) Assignee: The Procter & Gamble Company, Cincinnati, OH (US)

( * ) Notice: Subject to any disclaimer, the term of this patent is extended or adjusted under 35 U.S.C. 154(b) by 953 days.

(21) Appl. No.: 12/514,613

(22) PCT Filed: Nov. 12, 2007

(86) PCT No.: PCT/IB2007/054597
§ 371 (c)(1),
(2), (4) Date: Oct. 6, 2009

(87) PCT Pub. No.: WO2008/059435
PCT Pub. Date: May 22, 2008

(65) Prior Publication Data
US 2010/0178252 A1 Jul. 15, 2010

Related U.S. Application Data

(60) Provisional application No. 60/858,504, filed on Nov. 13, 2006, provisional application No. 60/932,880, filed on Jun. 1, 2007.

(51) Int. Cl.
| | | |
|---|---|---|
| *A61K 8/00* | (2006.01) |
| *A61Q 11/00* | (2006.01) |
| *A61K 6/00* | (2006.01) |
| *A61K 8/41* | (2006.01) |
| *A61K 8/21* | (2006.01) |
| *A61K 8/49* | (2006.01) |
| *A46B 7/04* | (2006.01) |
| *A46B 15/00* | (2006.01) |
| *A61B 5/00* | (2006.01) |

(52) U.S. Cl.
CPC .............. *A61K 8/498* (2013.01); *A46B 7/04* (2013.01); *A46B 15/0032* (2013.01); *A46B 15/0034* (2013.01); *A61B 5/0088* (2013.01); *A61Q 11/00* (2013.01); *A46B 2200/1066* (2013.01); *A61K 2800/434* (2013.01)

(58) Field of Classification Search
USPC ........................................ 424/49, 2.6, 54, 52
See application file for complete search history.

(56) References Cited

U.S. PATENT DOCUMENTS

| | | | |
|---|---|---|---|
| 3,261,978 A | 7/1966 | Brenman | |
| 3,309,274 A | 3/1967 | Brilliant | |
| 4,292,664 A | 9/1981 | Mack | |
| 4,348,378 A * | 9/1982 | Kosti | 424/9.71 |
| 4,400,372 A * | 8/1983 | Muhler et al. | 424/48 |
| 5,894,620 A | 4/1999 | Polaert et al. | |
| 6,902,397 B2 | 6/2005 | Farrell | |
| 2002/0119100 A1* | 8/2002 | Okada et al. | 424/9.7 |
| 2003/0036031 A1* | 2/2003 | Lieb et al. | 433/29 |
| 2003/0108488 A1 | 6/2003 | Rajaiah et al. | |
| 2003/0198605 A1 | 10/2003 | Montgomery | |
| 2004/0023184 A1 | 2/2004 | de Josselin de Jong et al. | |
| 2004/0091834 A1 | 5/2004 | Rizqiu et al. | |
| 2004/0106082 A1 | 6/2004 | Rizqiu et al. | |
| 2004/0147984 A1 | 7/2004 | Altshuler et al. | |
| 2004/0191729 A1 | 9/2004 | Altshuler et al. | |
| 2004/0193235 A1 | 9/2004 | Altshuler et al. | |
| 2004/0193236 A1 | 9/2004 | Altshuler et al. | |
| 2004/0204745 A1 | 10/2004 | Altshuler et al. | |
| 2004/0210276 A1 | 10/2004 | Altshuler et al. | |
| 2005/0053895 A1* | 3/2005 | Pinyayev et al. | 433/29 |
| 2005/0053898 A1 | 3/2005 | Ghosh et al. | |
| 2005/0064371 A1 | 3/2005 | Soukos et al. | |
| 2005/0091767 A1 | 5/2005 | Jimenez et al. | |
| 2005/0107849 A1 | 5/2005 | Altshuler et al. | |
| 2005/0170316 A1 | 8/2005 | Russell et al. | |
| 2005/0172429 A1 | 8/2005 | Russell et al. | |
| 2005/0175956 A1 | 8/2005 | Russell et al. | |
| 2005/0221251 A1 | 10/2005 | Soukos et al. | |
| 2006/0281042 A1* | 12/2006 | Rizoiu et al. | 433/29 |
| 2007/0237726 A1* | 10/2007 | White | A61K 8/19 424/49 |

FOREIGN PATENT DOCUMENTS

| | | |
|---|---|---|
| DE | 20 2004 001004 U1 | 3/2005 |
| JP | 60 075409 A | 4/1985 |
| WO | WO 92/06671 | 4/1992 |
| WO | WO 2005/123023 | 12/2005 |
| WO | WO 2005123023 | * 12/2005 |

OTHER PUBLICATIONS

International Search Report and Written Opinion for 10640Q dated Dec. 11, 2007.
CTFA International Cosmetic Ingredient Dictionary—Fourth edition, 1991, pp. 130, 136, 205-206.

* cited by examiner

*Primary Examiner* — Lezah Roberts
(74) *Attorney, Agent, or Firm* — Alexandra S. Anoff; George H. Leal

(57) ABSTRACT

An oral composition capable of identifying a condition within the oral cavity by causing a visual contrast between the condition and the hard and soft tissues of the oral cavity has at least one disclosing agent. The disclosing agent can fluoresce in order to highlight conditions within the oral cavity.

17 Claims, 10 Drawing Sheets

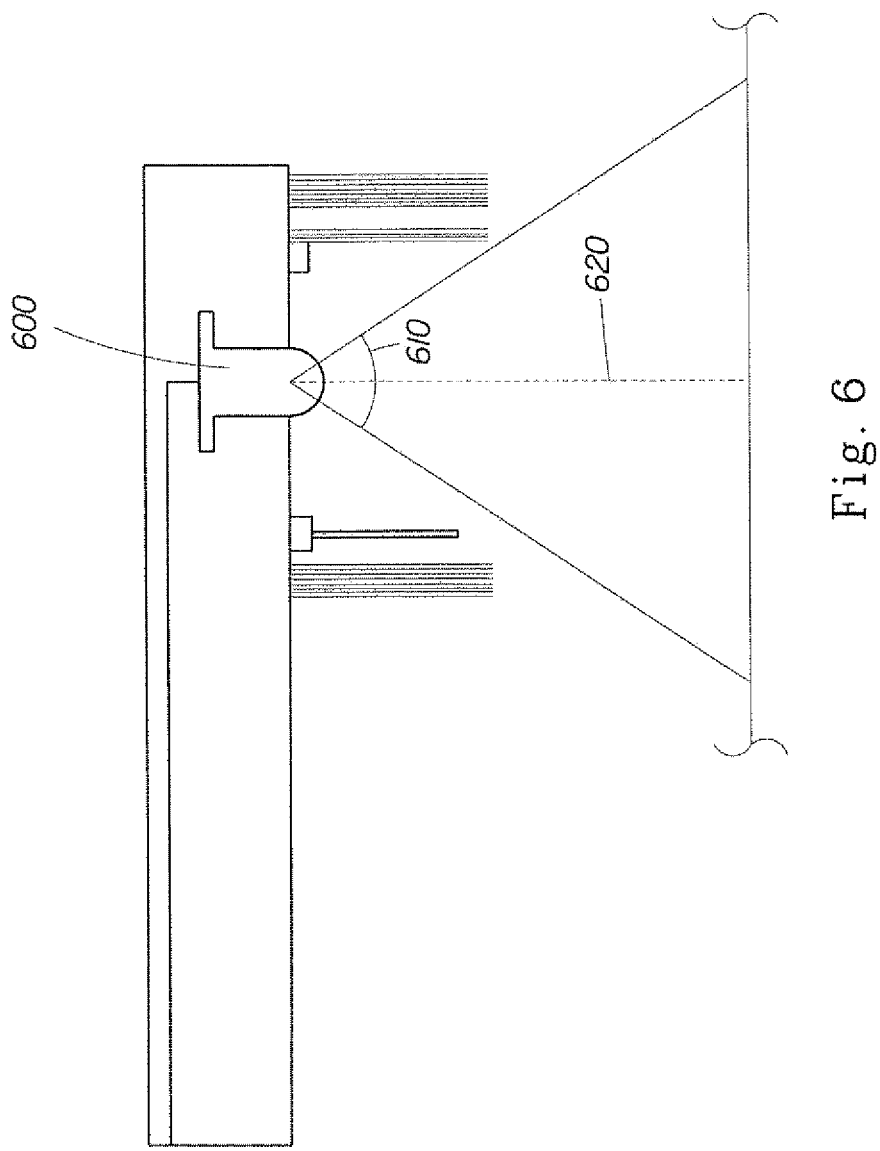

PRODUCTS AND METHODS FOR DISCLOSING CONDITIONS IN THE ORAL CAVITY

BACKGROUND OF THE INVENTION

This invention relates generally to a plaque disclosing system, and particularly to a dentifrice with a fluorescent dye and a lighted toothbrush that can illuminate residual dye in a user's mouth, as well as reduce visual indicia of dye staining on the toothbrush.

Although many innovations have been made in the field of oral health care, there is a continuing need for a system which can identify conditions, e.g. remaining dental plaque, within the oral cavity. Additionally, there is a need for a system which can facilitate the removal of some of these conditions, e.g. plaque removal.

SUMMARY OF THE INVENTION

Some aspects of the present invention pertain to oral compositions which include a disclosing agent capable of providing visual indication of an oral condition to a user and/or observer. The disclosing agent provides a visual contrast between the indicated condition and the surrounding oral tissues/surfaces.

Other aspects of the present invention pertain to instruments/devices which comprise an energy source. The energy source on the instrument/device is capable of supplying energy to a disclosing agent thereby activating the disclosing agent, thereby initiating the visual contrast.

Other aspects of the present invention pertain to kits which comprise at least one oral composition according to the present invention and at least one instrument/device according to the present invention. The kits of the present invention may be utilized to provide visual indication to the user and/or observer and to assist in the alleviation of the condition, e.g. removal of plaque, tartar, etc.

Other aspects of the present invention pertain to methods of identifying conditions within the oral cavity and/or methods of removal/alleviating the conditions within the oral cavity. For example, where an oral composition in accordance with the present invention is applied to the oral cavity, after a first brushing period, remaining plaque may be indicated as a condition. As such, a user/observer may rebrush the areas where remaining plaque is indicated, thereby removing the indicated condition.

BRIEF DESCRIPTION OF FIGURES

FIG. 6 is a partial side view showing a head of a toothbrush and a light angle for an LED in the head of the toothbrush;

DETAILED DESCRIPTION OF THE PREFERRED EMBODIMENTS

Definitions and Conventions

Figure 1A:
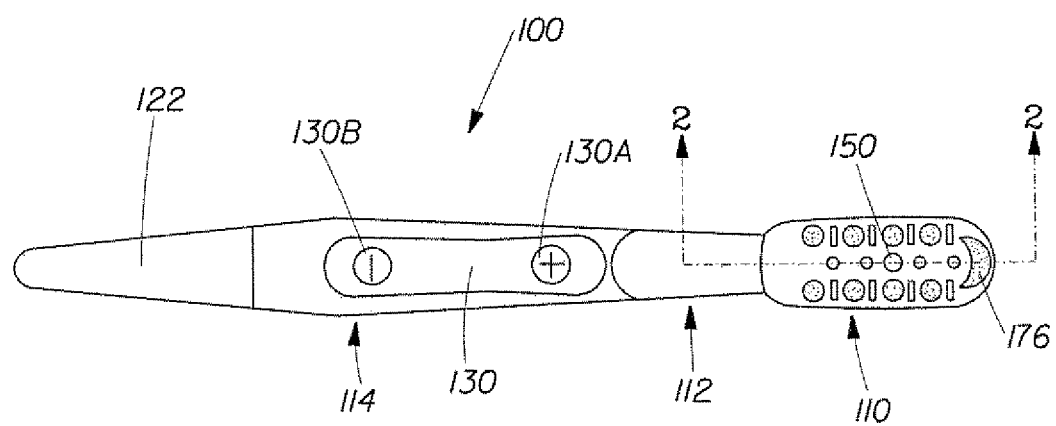
FIG. 1A is a plan view showing a toothbrush constructed in accordance with the present invention.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

"Compatible" in reference to an additional ingredient of a composition means that the additional ingredient can be commingled with the other ingredients of the composition without interaction in a manner which would substantially reduce the composition's stability and/or efficacy.

As used herein, the terms "oral condition" and "condition" are used to refer to dental plaque, tartar, debris, tooth decay, bio films, soft tissue abnormalities, soft tissue lesions, etc. within the oral cavity.

As used herein, the terms "plaque" and "dental plaque" are used to refer to a biofilm that builds up on teeth, on gingival tissue, oral hard tissue, and/or oral soft tissue.

"Plaque bacteria" means bacteria that causes plaque to form.

The term "dentifrice", as used herein, means paste, gel, powder, or liquid formulations unless otherwise specified, used to treat the surfaces of the oral cavity. The dentifrice composition may be a single phase composition or may be a combination of two or more separate dentifrice compositions. The dentifrice composition may be in any desired form, such as deep striped, surface striped, multilayered, having the gel surrounding the paste, a sheath/core arrangement, a co-extruded sheath/core arrangement, or any combination thereof. Each dentifrice composition in a dentifrice comprising two or more separate dentifrice compositions may be contained in a physically separated compartment of a dispenser and dispensed side-by-side or may be striped without physical separation.

As used herein, the term "disclosing agent" describes agents, elements, materials, compositions, or compounds, which indicate an oral condition to a user and/or an observer other than the user. For the purposes of the present invention, a "disclosing agent" can render conditions within the oral cavity more visible than non-conditions within the oral cavity.

The term "dispenser", as used herein, means any pump, tube, package, or container suitable for dispensing oral compositions.

As used herein the term "energy source" includes any electrically powered element that can convert electrical energy at the place where the element is disposed. For example, a light emitting element can convert electrical energy into light at the location where the element is disposed; such as on a head region of a toothbrush. As another example, a light emitting element can convert electrical energy into light at the location where the element is disposed and have the light transferred to another area of a device. For the purposes of the present invention, any suitable energy source may suffice, e.g. light emitting diodes, light-emitting elements using incandescent elements, laser elements, halogen elements, neon elements, fluorescent elements, plasma elements, xenon elements, flossing elements, massaging elements, scraping elements, heat emitting elements, sonic wave emitting elements, ultrasound emitting element, electric current emitting elements, composition emitting elements, infrared emitting elements, ultraviolet emitting elements, and/or any combination thereof.

"Fluoresces" describes the emission of energy, e.g. visible light, due to the absorption of energy.

"Fluorescing color" describes the color of agents, elements, materials, compositions, or compounds, while fluorescing.

"Fluorophore" describes agents, elements, materials, compositions, or compounds which "fluoresce" regardless of whether the emission of energy is essentially immediately after absorption of energy, coincident with the absorption of energy, or if the emission of energy is delayed after absorption of energy.

"Include" and its variants are non-limiting in the sense that recitation of items "included" in a list does not exclude other items.

"Marbled" refers to a striped design with a veined and/or mottled appearance similar to marble.

As used herein, the terms "microcapsule" and "microencapsulate" are used interchangeably to describe small capsules, typically having a diameter of less than 1000 microns which contain an active material, e.g. disclosing agent.

"Visually perceptible" means visible to a user or a third person.

"Ambient light" refers to the light normally encountered in a room, whether supplied by sunlight or lamps (i.e. light bulbs) used for conventional room lighting. Generally, ambient light includes the majority of or all wavelengths of the electromagnetic spectrum within the visible spectrum.

"Oral care composition" or "oral composition" means a product which in the ordinary course of usage can be retained in the oral cavity for contacting selected dental surfaces and/or oral tissues for purposes of oral activity. In addition to cleaning teeth to remove dental plaque, oral care compositions may be used to prevent formation of dental calculus and disorders such as caries, periodontitis and gingivitis, and also to eliminate and prevent oral malodor or halitosis and staining. Some examples of oral care product forms are toothpastes, dentifrices, tooth gels, subgingival gels, foams, mouthrinses, denture products, mouthsprays, lozenges, chewable tablets or chewing gums and strips or films for direct application or attachment to oral surfaces including any hard or soft oral tissues.

"Orally acceptable additive" means any additive which is now known, or hereinafter becomes known, as a safe and effective additive for an oral care composition. Examples include conventional additives in oral care compositions including but not limited to fluoride ion sources, anti-calculus or anti-tartar agents, desensitizing agents, teeth whitening agents such as peroxide sources, abrasives such as silica, herbal agents, chelating agents, buffers, anti-staining agents, alkali metal bicarbonate salts, thickening materials, humectants, water, surfactants, titanium dioxide, flavor system, sweetening agents, xylitol, coloring agents, and mixtures thereof.

"Preferentially indicates", in the context of a disclosing agent, means that in an oral cavity containing various different tissues (e.g., lips, tongue, gums), uncovered tooth enamel, tooth enamel covered by or encrusted with plaque, and optional dental work (e.g. amalgams, inlays, crowns, bridges, etc.), the disclosing agent indicates the presence of the conditions within the oral cavity when energy from an energy source is applied to the disclosing agent as opposed to indicating the entirety of the oral cavity.

"Stripes" or "ribbons" mean a phase in a composition which occupies a separate but distinct physical space inside a package in which it is stored, but is in direct contact with another "stripe". The stripes may be relatively uniform and even across the dimension of the package. Alternatively, the stripes may be uneven, e.g. wavy, or may be non-uniform in dimension. The stripes do not necessarily extend across the entire dimension of the package. The stripes may comprise various geometric patterns.

"Teeth" refers to one or more natural teeth as well as one or more artificial teeth or dental prosthesis.

"Visually distinctive" describes compositions that display visually different phases. These different phases are either distinctively separate or partially mixed as long as the multiple liquid phase composition remains visually perceptible.

The present invention provides products, systems, and methods for indicating conditions within the oral cavity. While the oral compositions described herein may disclose at least one of a number of conditions within the oral cavity, for the sake of simplicity, the discussion below will focus mainly on plaque and similar debris. Similarly, while the present invention contemplates the usage of any oral care device which can be equipped with an energy source, for the sake of simplicity, the discussion hereafter will focus on a toothbrush which is equipped with an energy source.

Oral Compositions

Disclosing Agents

The oral compositions of the present invention include a disclosing agent or a plurality of disclosing agents. The disclosing agent of the present invention can be utilized to provide visual indication of oral conditions to an observer and/or user. The visual indication of oral conditions to the observer and/or user can assist the observer and/or user in removal of the conditions or in identifying conditions which should be treated by a professional, e.g. dentist, oral surgeon, etc.

The disclosing agents of the present invention may visually indicate a condition within the oral cavity by providing a visual contrast between the conditions of the oral cavity and other tissues and surfaces within the oral cavity. For example, a disclosing agent may be selected such that when the disclosing agent is subjected to energy from an energy source, the disclosing agent fluoresces at locations of the oral conditions. Other examples of providing visual contrast are discussed hereafter. As a specific example, the disclosing agent may be applied to the oral cavity and visually highlight and/or indicate remaining plaque to a user and/or observer.

In some embodiments, any agents, materials, elements, compounds, or compositions, which will absorb light energy at a first range of wavelengths and, in response, emit light at second range of wavelengths can be a suitable disclosing agent, so long as it is safe for use in the manner intended here. In some embodiments, the first range of wavelengths may be different than the second range of wavelengths. For example, the disclosing agent may comprise a fluorophore.

Some examples of suitable disclosing agents include fluoroscein, dibromofluoroscein, tribromofluoroscein, tetrabromofluoroscein, other fluorescein derivatives (including salts thereof), xanthenes, pyrenes, e.g. pyranine, D&C Blue No. 1, D&C Blue No. 2, D&C Green No. 3, D&C Red No. 3, D&C Red No. 6, D&C Red No. 7, D&C Red No. 21, D&C Red No. 22, D&C Red No. 27, D&C Red No. 28, D&C Red No. 33, D&C Red No. 40, D&C Yellow No. 5, D&C Yellow No. 6, D&C Yellow No. 10, combinations thereof or any other dye approved for use in drugs and cosmetics by regulatory agencies such as, for example, The United States Food and Drug Administration. Other suitable disclosing agents may include dyes sold under the trade name Alexafluor™ by Invitrogen Corporation located in Carlsbad, Calif.

In embodiments where the disclosing agent comprises a fluorophore, the disclosing agent may be selected such that the disclosing agent fluoresces in response to electromagnetic energy having wavelengths which range from about 380 nm to about 780 nm, or any individual number within the range. In some embodiments, the disclosing agent may fluoresce in response to electromagnetic energy having wavelengths which are greater than about 380 nm, greater than about 390 nm, greater than about 400 nm, greater than about 410 nm, greater than about 420 nm, greater than about 430 nm, greater than about 440 nm, greater than about 450 nm, greater than about 460 nm, greater than about 470 nm, greater than about 480 nm, greater than about 490 nm, greater than about 500 nm, greater than about 510 nm, greater than about 520 nm, greater than about 530 nm, greater than about 540 nm, greater than about 550 nm, greater than about 560 nm, greater than about 570 nm, greater than about 580 nm, greater than about 590 nm, greater than about 600 nm, greater than about 610 nm, greater than about 620 nm, greater than about 630 nm, greater than about 640 nm, greater than about 650 nm, greater than about 660 nm, greater than about 670 nm, greater than about 680 nm, greater than about 690 nm, greater than about 700 nm, greater than about 710 nm, greater than about 720 nm, greater than about 730 nm, greater than about 740 nm, greater than about 750 nm, greater than about 760 nm and/or less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, less than about 410 nm, or less than about 400 nm.

In some embodiments, the disclosing agent may fluoresce in response to electromagnetic energy having wavelengths which are from about 400 nm to about 530 nm. For example, in one specific embodiment, the disclosing agent fluoresces in response to electromagnetic energy having a wavelength of about 470 nm. In other embodiments, the disclosing agent may fluoresce in response to electromagnetic energy having wavelengths between about 400 nm to about 440 nm. In other embodiments, the disclosing agent may fluoresce in response to electromagnetic energy having wavelengths between about 440 nm to about 530 nm. Additionally, embodiments are contemplated where the disclosing agent fluoresces in response to electromagnetic energy having wavelengths which are outside of the visible light spectrum, e.g. either higher or lower, combinations of higher and lower, and/or combinations of higher, lower, and visible spectrum. For example, embodiments are contemplated where the disclosing agent fluoresces in response to ultraviolet light, e.g. UVA about 315 nm to about 400 nm; UVB about 280 nm to about 315 nm; and/or UVC less than about 280 nm.

In some embodiments, the disclosing agent may emit electromagnetic energy having wavelengths of greater than about 400 nm. For example, disclosing agent useful in the present invention may emit electromagnetic energy having wavelengths which are greater than about 410 nm, greater than about 420 nm, greater than about 430 nm, greater than about 440 nm, greater than about 450 nm, greater than about 460 nm, greater than about 470 nm, greater than about 480 nm, greater than about 490 nm, greater than about 500 nm, greater than about 510 nm, greater than about 520 nm, greater than about 530 nm, greater than about 540 nm, greater than about 550 nm, greater than about 560 nm, greater than about 570 nm, greater than about 580 nm, greater than about 590 nm, greater than about 600 nm, greater than about 610 nm, greater than about 620 nm, greater than about 630 nm, greater than about 640 nm, greater than about 650 nm, greater than about 660 nm, greater than about 670 nm, greater than about 680 nm, greater than about 690 nm, greater than about 700 nm, greater than about 710 nm, greater than about 720 nm, greater than about 730 nm, greater than about 740 nm, greater than about 750 nm, greater than about 760 nm and/or less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, or less than about 410 nm.

While fluorescing, the disclosing agent may absorb energy from the energy source where the energy has a first range of wavelengths having a first band maxima ($\lambda_A$) and may emit energy at a second range of wavelengths having a second band maxima ($\lambda_E$). The difference (in frequency or wavelength) between ($\mu_E$) and ($\lambda_A$) is termed the emission-absorbence shift. In some embodiments, the emission-absorbance shift of the disclosing agent can be greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 125 nm, greater than about 150 nm, greater than about 200 nm, greater than about 250 nm, greater than about 300 nm, greater than about 350 nm, greater than about 375 nm and/or less than about 400, less than about 375 nm, less than about 350 nm, less than about 300 nm, less than about 250 nm, less than about 200 nm, less than about 150 nm, or less than about 100 nm. The emission-absorbance shift can be the same as the Stokes shift for the disclosing agent when $\lambda_A$ is equal to the excitation maxima of the disclosing agent.

Additionally, in some embodiments, a disclosing agent may be selected such that the disclosing agent absorbs applied energy and emits or reflects very little energy. This may cause the indicated areas to look dark versus other oral cavity surfaces being lighter. These embodiments may also provide visual distinction to the observer. In such embodiments, the energy source which applies energy to the disclosing agent can be matched with the absorbance of the disclosing agent. Accordingly, the light reflected from oral surfaces may be visually distinct from the areas of indication because the areas of indication will absorb the applied energy and the remaining oral surfaces may reflect a large portion of the energy applied.

Embodiments are similarly contemplated where the disclosing agent reflects a large portion of energy while the oral cavity surfaces reflect less energy. In these embodiments, the conditions indicated by the disclosing agent may appear lighter than the surrounding oral cavity surfaces.

In order to provide visual indication of an oral condition, in some embodiments, the reflected and emitted energy from the indicated condition and the reflected and emitted energy from other oral cavity surfaces may be visually distinct. For example, in some embodiments where the applied wavelength of energy from the energy source is about 470 nm, the reflected energy and emitted energy from a portion of the surface of the tooth may be about 470 nm, i.e. blue. However, the disclosing agent may reflect and emit energy at a wavelength of about 550 nm, i.e. yellow. The absolute value of the difference in maxima of the wavelengths between the reflected energy and the emitted energy is termed the reflectance-emission shift (RES):

$$ABS|\lambda_{OC}-\lambda_{DA}|=RES$$

where $\lambda_{OC}$ a maximum wavelength of the reflected and/or emitted energy from other oral cavity surfaces, and where $\lambda_{DA}$ is the wavelength of the reflected and/or emitted energy from the disclosing agent.

In general, the wavelength of the reflected and emitted energy from the other oral cavity surfaces may be similar to the wavelength of the energy which is introduced into the oral cavity via the energy source. Accordingly, $\lambda_{OC}$ may be equal to $\lambda_A$ described heretofore. Similarly, the wavelength of the reflected and emitted energy from the disclosing agent may be similar to the wavelength of the disclosing agent described heretofore, e.g. $\lambda_{DA}$ may be equal to $\lambda_E$.

The RES can have a value similar to that described with regard to the emission-absorbence shift described previously. Additionally, the RES can be applicable to embodiments where the disclosing agent emits or reflects energy or where the disclosing agent emits or reflect very little of the applied energy as described above.

Additionally, there may be more than one RES shift. For example, if there are distinct reflectance and an emission maxima from the oral cavity surfaces, more than one RES shift may exist.

Aside from the measurement of the wavelengths reflected and/or emitted either from the oral cavity or the disclosing agent, under the same applied energy source, the reflected/emitted energy from a portion of the tooth can be a first color while the reflected/emitted energy from the disclosing agent is a second color. The first color is different than the second color. For example, the first color may be perceptibly lighter than or perceptibly darker than the second color. As another example, the difference between the first color and the second color may be a perceptible color contrast, e.g. the first color may be blue while the second color is yellow. Accordingly, the present invention is capable of providing a visual contrast to the user and/or observer between oral conditions and the remainder of the oral cavity.

The concentration of the disclosing agent in the oral composition can be selected so that the conditions within the oral cavity are not readily visually perceptible under ambient light but becomes more visually perceptible when electromagnetic energy is applied to the oral cavity from an energy source. Note that the electromagnetic energy supplied by the energy source may be in addition to the ambient light or may be in the absence of ambient light. Thus, the concentration of the disclosing agent may depend, in part, on the particular disclosing agent selected, with possibly lesser amounts being needed for disclosing agent absorbing or outputting greater light intensity and conversely. Additionally, the concentration of the disclosing agent may depend, in part, on the oral condition to be identified, the ability of the disclosing agent to be incorporated into the specific carrier, e.g. mouthrinse, dentifrice, etc., and where the condition to be identified is plaque, the ability of the disclosing agent to attach, diffuse into, bind with, saturate, etc., to the plaque.

In some embodiments, the concentration of the disclosing agent in the oral composition may range from about 0.001% by weight to about 5% by weight, or any individual number within the range. In some embodiments, the concentration of the disclosing agent can be greater than about 0.001% by weight, greater than about 0.003% by weight, greater than about 0.005% by weight, greater than about 0.007% by weight, greater than about 0.009% by weight, greater than about 0.01% by weight, greater than about 0.02% by weight, greater than about 0.03% by weight, greater than about 0.04% by weight, greater than about 0.05% by weight, greater than about 0.06% by weight, greater than about 0.07% by weight, greater than about 0.08% by weight, greater than about 0.09% by weight, greater than about 0.1% by weight, greater than about 0.165% by weight, greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 1.5% by weight, greater than about 2% by weight, greater than about 2.5% by weight, greater than about 3% by weight, greater than about 3.5% by weight, greater than about 4% by weight, greater than about 4.5% by weight and/or less than about 5% by weight, less than about 4.5% by weight, less than about 4% by weight, less than about 3.5% by weight, less than about 3% by weight, less than about 2.5% by weight, less than about 2% by weight, less than about 1.5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.09% by weight, less than about 0.08% by weight, less than about 0.07% by weight, less than about 0.06% by weight, less than about 0.05% by weight, less than about 0.04% by weight, less than about 0.03% by weight, less than about 0.02% by weight, or less than about 0.01% by weight.

Carriers

In addition to the disclosing agent, the inventive oral care compositions may include a carrier for delivering this disclosing agent to the teeth to be treated. The particular carrier to be used may be determined by the way the composition is to be introduced into the oral cavity. For example, where the carrier is a toothpaste or tooth gel, the carrier materials for toothpaste, tooth gel or the like may include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer.

As another example, oral compositions in accordance with the present invention may be in the form of dentifrices, such as toothpastes and tooth powders. Carrier materials of such dentifrices may include one or more of a dental abrasive (from about 6% to about 50%), a surfactant (from about 0.01% to about 10%), a thickening agent (from about 0.05% to about 5%), a humectant (from about 10% to about 55%), a flavoring agent (from about 0.04% to about 2%), a sweetening agent (from about 0.1% to about 3%), and water (from about 2% to about 45%). Such toothpaste or tooth gel may also include one or more of an anticaries agent (from about 0.05% to about 0.3% as fluoride ion), an anticalculus agent (from about 0.1% to about 13%), and other orally acceptable additives, as further discussed below. Tooth powders, of course, contain substantially all non-liquid components.

As yet another example, oral compositions in accordance with the present invention may include mouthwashes, rinses, and mouth sprays. Carrier materials of such mouthwashes, rinses, and mouth sprays, may include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), and a sweetening agent (from about 0.1% to about 3%). Such mouthwashes and mouth sprays may also include one or more of an anticaries agent (from about 0.05% to about 0.3% as fluoride ion), an anticalculus agent (from about 0.1% to about 3%), and other orally acceptable additives, as further discussed below. See, for example, U.S. Pat. No. 3,988,433 to Benedict.

As yet another example, oral care compositions in accordance with the present invention may be in the form of non-abrasive gels and subgingival gels, which may be aqueous or non-aqueous. Carrier materials of aqueous gels may include water, a thickening agent (from about 0.1% to about 20%), a humectant (from about 0.01% to about 55%), a flavoring agent (from about 0.001% to about 2%), or a sweetening agent (from about 0.1% to about 3%). The compositions may comprise an anticaries agent (from about 0.001% to about 0.3% as fluoride ion), an anticalculus agent (from about 0.005% to about 13%), and other orally acceptable additives, as further discussed below. For subgingival gels used for delivery of actives into the periodontal pockets or around the periodontal pockets, a "subgingival gel carrier" may be chosen as disclosed in, e.g. U.S. Pat. Nos. 5,198,220 and 5,242,910, issued Mar. 30, 1993 and Sep. 7, 1993, respectively both to Damani.

As yet another example, oral compositions in accordance with the present invention may include lozenges. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents.

As yet another example, the oral compositions in accordance with the present invention may also be in the form of dental solutions and irrigation fluids. Carrier materials of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%), and other orally acceptable additives, as further discussed below.

Oral compositions in accordance with the present invention may comprise any suitable carrier or carrier material. Some examples of suitable carriers for use in oral care compositions in accordance with the invention are described in U.S. Pat. No. 5,288,480; U.S. Pat. No. 5,288,480; U.S. Pat. No. 5,344,641; U.S. Pat. No. 4,855,155; U.S. Pat. No. 6,696,045; U.S. Pat. No. 5,939,052; U.S. Pat. No. 6,740,311; U.S. Patent Application Publication No. 2006/0134018; 2006/0134018; 2006/0141039; 2006/0140883; 2005/0112070; 2004/0126334; and 2005/0169852.

The inventive oral care composition may have a pH ranging from about 4.0 to about 11, or any individual number within the range. In a number of embodiments, the pH of the compositions can be greater than about 4, greater than about 4.5, greater than about 5, greater than about 5.5, greater than about 6, greater than about 6.5, greater than about 7, greater than about 7.5, greater than about 8, greater than about 8.5, greater than about 9, greater than about 9.5, greater than about 10, greater than about 10.5 and/or can be less than about 11, less than about 10.5, less than about 10, less than about 9.5, less than about 9, less than about 8.5, less than about 8, less than about 7.5, less than about 7, less than about 6.5, less than about 6, less than about 5.5, less than about 5, or less than about 4.5. The pH of a dentifrice composition is measured from a 3:1 aqueous slurry of the dentifrice, e.g., 3 parts water to 1 part toothpaste.

The pH can play a role in the solubility of the disclosing agent within the oral care composition. Additionally, the pH may also impact the stability of the disclosing agent within the oral care composition.

Colorants

The disclosing agent used in particular embodiments of the inventive oral care compositions may be selected to emit light whose color is different from the color of the oral care composition as a whole when viewed under ambient light. The disclosing agent may or may not impart color to the composition. In cases where the disclosing agent does impart color to the inventive oral care composition an additional colorant for imparting a different overall particular color to the oral care composition may be included.

The difference in wavelengths between a colorant of the oral composition (as determined via absorbance) and the color of the disclosing agent (as determined by absorbance) is termed the compositional shift. The colorant of the oral composition has a first wavelength having a first band maxima (determined via absorbance) and the color of the disclosing agent, has a second wavelength having a second band maxima. The absolute value of the difference (in frequency or wavelength) between the first band maxima of the colorant and the second band maxima of the disclosing agent is the compositional shift (CS):

$$ABS|\lambda_C-\lambda_D|=CS$$

where $\lambda_C$ is the first band maxima of the colorant of the oral composition, and where $\lambda_D$ is the second band maxima of the disclosing agent.

Note that in some embodiments, $\lambda_D$ may be greater than $\lambda_D$ while in other embodiments, $\lambda_C$ may be greater than $\lambda_D$. For example, a disclosing agent having an absorbance maxima at 430 nm and a colorant having an absorbance maxima at 630 nm can be combined to produce and overall composition which is green rather than yellowish or orangish depending on the concentration of the disclosing agent.

In some embodiments, the compositional shift can be greater than about 10 nm, greater than about 25 nm, greater than about 50 nm, greater than about 75 nm, greater than about 100 nm, greater than about 125 nm greater than about 150 nm, greater than about 200 nm, greater than about 250 nm, greater than about 300 nm, greater than about 350 nm, greater than about 375 nm and/or less than about 400, less than about 375 nm, less than about 350 nm, less than about 300 nm, less than about 250 nm, less than about 200 nm, less than about 150 nm, or less than about 125 nm, less than about 100 nm, less than about 50 nm, less than about 25 nm, less than about 10 nm. The compositional shift can be measured to the left or to the right of absorbence maxima of the disclosing agent.

Additionally, the color of the overall oral care composition may or may not correspond to the fluorescing color of the disclosing agent when activated with the energy source. For example, a pyranine containing dentifrice (without any additional coloring agent) may appear yellow and similarly may fluoresce yellow under blue light illumination to indicate a condition. Yet the composition color of yellow may not be attractive to consumers. Therefore an additional blue colorant can be added to the composition to make the overall composition color appear green and compatible with mint flavors which may be preferred by consumers. Conversely, a disclosing agent which fluoresces blue when activated with the energy source may be more suited to an overall composition color which appears blue. In this case an additional colorant may or may not be needed. Methods of enhancing the color of the oral composition and/or the color of the disclosing agent are discussed hereafter.

The particular color of the oral composition can be altered by the compositional shift described above. For example, if the absorbance maxima of the disclosing agent were distributed about 650 nm, then the addition of a colorant which has a color absorbance distributed about 430 nm could be added to the oral composition to modify the compositional shift of the oral composition.

Embodiments are contemplated where at least one additional colorant is added to the oral composition. In such embodiments, there may be an additional compositional shift. For example, where a first colorant and a second colorant have properties which result in different absorbances of light (as determined via absorbance), a second compositional shift may exist relative to the disclosing agent. The second compositional shift may be as described above. Accordingly, embodiments having more than one compositional shift and/or more than one colorant are contemplated. The second composition shift, if any, can be in a similar range to those disclosed with regard to the first compositional shift.

For this purpose, the inventive oral care compositions many include any suitable colorant. Some examples include D&C Blue No. 1, D&C Blue No. 2, D&C Green No. 3, D&C Red No. 3, D&C Red No. 6, D&C Red No. 7, D&C Red No. 21, D&C Red No. 22, D&C Red No. 27, D&C Red No. 28, D&C Red No. 33, D&C Red No. 40, D&C Yellow No. 5, D&C Yellow No. 6, D&C Yellow No. 10, combinations thereof or any other dye approved for use in drugs and cosmetics by regulatory agencies such as, for example, The United States Food and Drug Administration. In some embodiments, the coloring agent may be non-fluorescing. Other examples may include FD&C colorants and other D&C colorants.

In some embodiments, at least one of the colorants may include a fluorophore as described above ("secondary disclosing agent"). In this instance, the secondary disclosing agent may exhibit light in the visible spectrum whose color is substantially different from the color of the light emitted by the primary disclosing agent, as described above. As such, embodiments are contemplated where a system may include a second energy source which emits energy to elicit a separate response from the secondary disclosing agent. For example, the second energy source may cause the secondary disclosing agent to emit a color having a wavelength which is greater than or less than that of the wavelength emission of the primary disclosing agent.

Additionally, embodiments are contemplated where the primary disclosing agent and the second disclosing agent can be utilized to identify separate conditions utilizing a single energy source or utilizing multiple energy sources. For example, the primary disclosing agent may be utilized to identify plaque while the secondary disclosing agent can be utilized to identify caries. In some embodiments, when electromagnetic energy is applied to the primary and secondary disclosing agents, the primary disclosing agent may emit a first response and the secondary disclosing agent may emit a second response.

If the first response and the second response are elicited contemporaneously and/or are expected to be viewed contemporaneously, then the wavelength of the color of the first response and the wavelength of the color of the second response can be different. For example, the difference between the wavelength of the first response and the wavelength of the second response may range from about 10 nm to about 400 nm, or any individual number within the range. The absolute value of the difference (in wavelength) between the first band maxima of the first response and the second band maxima of the second response is the emission shift (ES):

$$ABS|\lambda_{FR}-\lambda_{SR}|=ES$$

where $\lambda_{FR}$ is the first band maxima of the first response and is equal to $\lambda_E$ described above, and where $\lambda_{SR}$ is the second band maxima of the second response.

In some embodiments, the ES may be greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 110 nm, greater than about 120 nm, greater than about 130 nm, greater than about 140 nm, greater than about 150 nm, greater than about 160 nm, greater than about 170 nm, greater than about 180 nm, greater than about 190 nm, greater than about 200 nm, greater than about 210 nm, greater than about 220 nm, greater than about 230 nm, greater than about 240 nm, greater than about 250 nm, greater than about 260 nm, greater than about 270 nm, greater than about 280 nm, greater than about 290 nm, greater than about 300 nm, greater than about 310 nm, greater than about 320 nm, greater than about 330 nm, greater than about 340 nm, greater than about 350 nm, greater than about 360 nm, greater than about 370 nm, greater than about 380 nm, greater than about 390 nm, and/or less than about 400 nm, less than about 390 nm, less than about 380 nm, less than about 370 nm, less than about 360 nm, less than about 350 nm, less than about 340 nm, less than about 330 nm, less than about 320 nm, less than about 310 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, or less than about 20 nm.

Additionally, as described above, a second energy source may be utilized to excite the secondary disclosing agent. In such embodiments, a first energy source may be utilized to elicit a first response and subsequently, the second energy source may be utilized to elicit a second response, or vice versa. In some embodiments, the ES may be equal to about zero. In some embodiments, the ES may be as described above.

The amount of colorant to be included in particular embodiments of the inventive oral care compositions can vary widely and may depend, on the particular colorant employed. In some embodiments, a sufficient amount may be an amount which produces a distinctive color in the oral care composition which can be readily distinguished from the fluorescing color of the disclosing agent.

Normally, this means that the inventive oral care composition may contain about 0.001% by weight to about 5% by weight of additional colorant, or any individual number within the range. In some embodiments, the concentration of the additional colorant can be greater than about 0.001% by weight, greater than about 0.005% by weight, greater than about 0.007% by weight, greater than about 0.009% by weight, greater than about 0.01% by weight, greater than about 0.02% by weight, greater than about 0.03% by weight, greater than about 0.04% by weight, greater than about 0.05% by weight, greater than about 0.06% by weight, greater than about 0.07% by weight, greater than about 0.08% by weight, greater than about 0.09% by weight, greater than about 0.1% by weight, greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 1.5% by weight, greater than about 2% by weight, greater than about 2.5% by weight, greater than about 3% by weight, greater than about 3.5% by weight, greater than about 4% by weight, greater than about 4.5% by weight and/or less than about 5% by weight, less than about 4.5% by weight, less than about 4% by weight, less than about 3.5% by weight, less than about 3% by weight, less than about 2.5% by weight, less than about 2% by weight, less than about 1.5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.09% by weight, less than about 0.08% by weight, less than about 0.07% by weight, less than about 0.06% by weight, less than about 0.05% by weight, less than about 0.04% by weight, less than about 0.03% by weight, less than about 0.02% by weight, or less than about 0.01% by weight.

The addition of a colorant or multiple colorants to an oral composition may be utilized to modify the overall color of the oral composition, as stated previously. For example, where the disclosing agent appears yellow under ambient light, colorants may be added to produce an overall oral composition having a green color. Where the oral composition comprises a dentifrice there are many different ways of enhancing or modifying the color of the dentifrice.

In some embodiments, the disclosing agent may be within a dentifrice dispenser in a striped form. Any suitable method known in the art can be utilized to impart stripes and/or layers to the dentifrice of the present invention. An example of such a method is disclosed in U.S. Patent Application Ser. No. 60/473,692 filed on Jul. 16, 2003, entitled "Visually distinctive multiple liquid phase compositions". In these embodiments, there is internal striping within the dentifrice with no separation between the phases, e.g. the disclosing agent and the remaining dentifrice. Despite the color of the disclosing agent, the striped pattern either in the dispenser or as it is dispensed on an oral care device, may make the color of the disclosing agent more palatable for consumers.

Alternatively, embodiments are contemplated where the disclosing agent and the remainder of the dentifrice are contained within the dispenser but are physically separated. Accordingly, the disclosing agent and the remainder of the dentifrice can be dispensed in a striped pattern onto an oral care device.

Additionally, embodiments are contemplated where the disclosing agent and the remainder of the dentifrice are dispensed in a concentric manner. For example, the disclosing agent could be dispensed within a sheath that is the remainder of the dentifrice. In this manner, the disclosing agent may not be visually perceptible as dispensed. For the concentric embodiments, the disclosing agent and the remainder of the dentifrice may be physically separated within the dispenser. Alternatively, in some embodiments, there may be no physical separation between the disclosing agent and the remainder of the dentifrice.

Regardless of whether the disclosing agent and the remainder of the dentifrice is physically separated or not, the dentifrice should be packaged such that a sufficient amount of the disclosing agent is dispensed. For example, the ratio of the volume percentage of the disclosing agent to the remainder of the dentifrice can be from about 1:99 to about 99:1, or any individual ratio within the range. In some embodiments, the ratio of the volume percentage of the disclosing agent to the remainder of the dentifrice can be from about 1:99, greater than about 1:50, greater than about 1:25, greater than about 1:20, greater than about 1:15, greater than about 1:10, greater than about 1:7, greater than about 1:5, greater than about 1:3, greater than about 1:2, greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1 and/or less than about 99:1, less than about 90:1, less than about 80:1, less than about 70:1, less than about 60:1, less than about 50:1, less than about 40:1, less than about 30:1, less than about 20:1, less than about 10:1, less than about 9:1, less than about 8:1, less than about 7:1, less than about 6:1, less than about 5:1, less than about 4:1, less than about 3:1, less than about 2:1, less than about 1:1, less than about 1:2, less than about 1:3, less than about 1:5, less than about 1:7, less than about 1:10, less than about 1:15, less than about 1:20, less than about 1:25, or less than about 1:50.

Additionally, embodiments are contemplated where each of the phases include some of the disclosing agent. For example, a first phase of disclosing agent could comprise a large weight percentage of disclosing agent while a second phase of carrier could comprise a smaller weight percentage of disclosing agent. Accordingly, in some embodiments where the disclosing agent is green, the first phase could appear as a dark green color while the second phase may appear as a lighter green. Alternatively, where the disclosing agent is blue, the first phase may appear as a dark red color while the second phase appears as a light red or pink color. These embodiments are applicable whether the phases are physically separated within the dispenser or not.

Moreover, embodiments are contemplated where the dentifrice comprises a disclosing agent and a colorant. In these embodiments, the disclosing agent can be the first phase, the carrier can be the second phase, and the colorant can be the third phase. In some embodiments, the first phase and the second phase may be configured as described above. However, the third phase may be placed between the two phases as a concentric sheath around the first phase and/or the second phase. Additionally, embodiments are contemplated where the disclosing agent and/or the colorant are added to the first, second, and/or the third phases to provide some color change within these phases. Similarly, embodiments are contemplated where the dentifrice comprises multiple disclosing agents and/or multiple colorants.

In some embodiments, the disclosing agent and/or the colorant may be microencapsulated in a polymeric shell. Accordingly, during brushing or swishing of the oral composition, the polymeric shell can break thereby releasing the disclosing agent and/or colorant to the oral cavity. For example, an oral composition in accordance with the present invention may comprise a plurality of microcapsules which contain disclosing agent.

One type of capsule, referred to as a wall or shell capsule, comprises a generally spherical hollow shell of material, typically polymer material, within which the disclosing agent is contained. The shell capsules may be prepared using a range of conventional methods known to those skilled in the art for making shell capsules such as coacervation, interfacial polymerization and poly-condensation.

The process of coacervation typically involves encapsulation of a generally water-insoluble material by the precipitation of colloidal material(s) onto the surface of droplets of the material. Coacervation may be simple e.g. using one colloid such as gelatin, or complex where two or possibly more colloids of opposite charge, such as gelatin and gum arabic or gelatin and carboxymethyl cellulose, are used under carefully controlled conditions of pH, temperature and concentration. Coacervation techniques are described, e.g. in U.S. Pat. No. 2,800,458; U.S. Pat. No. 2,800,457; GB Patent No. 929,403; EP 385,534; and EP 376,385. It is recognized however that many variations with regard to materials and process steps are possible.

Interfacial polymerization produces encapsulated shells from the reaction of at least one oil-soluble wall forming material present in the oil phase with at least one water-soluble wall forming material present in the aqueous phase. A polymerization reaction between the two wall-forming materials occurs resulting in the formation of covalent bonds at the interface of the oil and aqueous phases to form the capsule wall. An example of a shell capsule produced by this method is a polyurethane capsule.

Polycondensation involves forming a dispersion or emulsion of water-insoluble material (a non-limiting example of which is perfume) in an aqueous solution of precondensate of polymeric materials under appropriate conditions of agitation to produce capsules of a desired size, and adjusting the reaction conditions to cause condensation of the precondensate by acid catalysis, resulting in the condensate separating from solution and surrounding the dispersed water-insoluble material fill to produce a coherent film and the desired micro-capsules. Polycondensation techniques are described, in U.S. Pat. No. 3,516,941; U.S. Pat. No. 4,520,142; U.S. Pat. No. 4,528,226; U.S. Pat. No. 4,681,806; U.S. Pat. No. 4,145,184; GB Patent No. 2,073,132 and PCT Publication WO 99/17871. It is recognized however that many variations with regard to materials and process steps are possible.

Nonlimiting examples of materials suitable for making the shell of the microcapsule include urea-formaldehyde, melamine-formaldehyde, phenol-formaldehyde, gelatin, gum arabic, polyurethane, polyamides, methyl cellulose and other cellulose derivatives, cellulose esters including cellulose butyrate, acetate and cellulose nitrate, cellulse ethers like ethyl cellulose, polymethacrylates, polymethacrylic acid, polyacrylic acid, polyacrylates, polyvacrylamide, polyacryldextran, polyalkyl cyanoacrylate, cellulose acetate, cellulose acetate butyrate, cellulose nitrate, nylong 6, polyteraphthalamide and other polyamides, polyvinyl alcohol, polyvinylpyrollidone, shellac, polycaprolactones, polydimethylsiloxanes, and other siloxanets, aliphatic and aromatic polyesters, polyethylene oxid, polyethylene-vinyl acetate, polyglycolic acid, polylactic acid, and copolymers, poly (methyl vinyl ether/maleic anhydride), polystyrene, polyvinyl acetate phthalate, starch, sol-gels, micro-encapsulating material used for liquid crystals, micro-encapsulating materials used for thermochromic leuco dyes, micro-encapsulating materials used for photo-chromic dyes, low and high melting waxes such as paraffin, beeswax, carnauba wax, and the like. One particularly suitable example of a material suitable for making a microcapsule are cyclodextrins such as CAVAMAX® available from International Specialty Products located in Wayne, N.J. Other encapsulation techniques are disclosed in *MICROENCAPSULATION: Methods and Industrial Applications*, Edited by Benita and Simon (Marcel Dekker, Inc., 1996).

Many of the materials for the microcapsules may be clear or opaque. For example, where the microcapsule material is gelatin, the microcapsule may be clear or opaque. Encapsulating gelatins can be dissolved or ruptured during brushing and/or swishing of the oral composition within the oral cavity, thereby releasing the disclosing agent and/or colorant to the tissues, surfaces, etc. within the oral cavity.

One preferred method for forming shell capsules useful herein is polycondensation, which may be used to produce aminoplast encapsulates. Aminoplast resins are the reaction products of one or more amines with one or more aldehydes, typically formaldehyde. Non-limiting examples of suitable amines include urea, thiourea, melamine and its derivates, benzoguanamine and acetoguanamine and combinations of amines. Suitable cross-linking agents (e.g. toluene diisocyanate, divinyl benzene, butane diol diacrylate etc.) may also be used and secondary wall polymers may also be used as appropriate, as described in the prior art e.g. anhydrides and their derivatives, particularly polymers and co-polymers of maleic anhydride as disclosed in PCT Publication WO 02/074430.

Preferably, the shell capsules are aminoplast capsules, more preferably based on melamine, singly or in combination with other suitable amines, crosslinking agents and secondary polymers. The disclosing agents and/or colorants may be encapsulated either in liquid or dried form within the microcapsules. Particles and capsule diameter can vary from about 10 nanometers to about 1000 microns, or from about 50 nanometers to about 100 microns, or from about 1 micron to about 60 microns. The particle size distribution can be narrow, broad or multimodal.

Fluoride Source

It is common to have a water-soluble fluoride compound present in dentifrices and other oral compositions in an amount sufficient to give a fluoride ion concentration in the composition, and/or when it is used of from about 0.0025% to about 5.0% by weight, or any individual number within the range. In some embodiments, fluoride may be present from about 0.005% to about 2% by weight, to provide anticaries effectiveness. A wide variety of fluoride ion-yielding materials can be employed as sources of soluble fluoride in the present compositions. Some examples of suitable fluoride ion-yielding materials are described in U.S. Pat. No. 3,535,421, Oct. 20, 1970 to Briner et al. and U.S. Pat. No. 3,678,154, Jul. 18, 1972 to Widder et al. Some examples of fluoride ion sources include: stannous fluoride, sodium fluoride, potassium fluoride, sodium monofluorophosphate, indium fluoride and many others. In some specific embodiments, stannous fluoride and/or sodium fluoride may be utilized, as well as mixtures thereof.

Stain Mitigators

In some embodiments, the inventive oral care compositions may comprise a stain mitigator. Some suitable examples of stain mitigators include hexametophosphate, phytic acid, polyphosphate, pyrophosphate, or combinations thereof. Stain mitigators may be beneficial in oral compositions which include stannous fluoride.

Teeth Whitening Actives

Teeth whitening actives may also be included in the inventive oral care compositions. The actives suitable for whitening include the peroxides, metal chlorites, perborates, percarbonates, peroxyacids, persulfates, and combinations thereof. Some examples of suitable peroxide compounds include hydrogen peroxide, urea peroxide, calcium peroxide, and mixtures thereof. Some examples of suitable metal chlorites include calcium chlorite, barium chlorite, magnesium chlorite, lithium chlorite, sodium chlorite, and potassium chlorite. A preferred chlorite is sodium chlorite. Additional whitening actives may be hypochlorite and chlorine dioxide. A preferred percarbonate is sodium percarbonate. Examples of other suitable whitening agents include potassium, ammonium, sodium and lithium persulfates and perborate mono- and tetrahydrates, and sodium pyrophosphate peroxyhydrate.

Anticalculus Agent

The inventive oral care compositions may optionally include an additional anticalculus agent, such as a pyrophosphate salt as a source of pyrophosphate ion. Some examples of pyrophosphate salts useful in the present compositions include the dialkali metal pyrophosphate salts, tetraalkali metal pyrophosphate salts, and mixtures thereof. Examples of other suitable pyrophosphate salts include disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a suitable pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used. The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include, for example, such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), polyphosphates (e.g., tripolyphosphate and hexametaphosphate), diphosphonates (e.g., EHDP; AHP), polypeptides (such as polyaspartic and polyglutamic acids), and mixtures thereof.

Some examples of phosphonate copolymers include the diphosphonate-derivatized polymers in U.S. Pat. No. 5,011,913 to Benedict et al, such as diphosphonate modified polyacrylic acid. Other suitable examples of phosphonate-containing polymers are described in U.S. Pat. No. 5,980,776 to Zakikhani, et al.

Polyphosphates may also be included in the present compositions. A polyphosphate is generally understood to consist of two or more phosphate groups arranged primarily in a linear configuration, although some cyclic derivatives may be present. In addition to pyrophosphates and tripolyphosphate, which are technically polyphosphates, also desired are the polyphosphates having an average of about four or more phosphate groups, i.e., tetrapolyphosphate and hexametaphosphate, among others. Polyphosphates larger than tetrapolyphosphate usually occur as amorphous glassy materials, the linear "glassy" polyphosphates having the formula:

wherein X is sodium or potassium and n averages from about 6 to about 125. Examples of suitable polyphosphates are manufactured by FMC Corporation which are commercially known as Sodaphos (n≈6), Hexaphos (n≈13), and Glass H (n≈21). These polyphosphates may be used alone or in combination thereof.

Abrasives

Dental abrasives useful in the inventive oral care compositions include many different materials. The material selected should be one which is compatible within the composition of interest and does not excessively abrade dentin. Some examples of suitable abrasives include silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Some examples of suitable resins include melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types can provide unique benefits of exceptional dental cleaning and polishing performance without unduly abrading tooth enamel or dentine. The silica abrasive polishing materials herein, as well as other abrasives, may have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, and U.S. Pat. No. 6,740,311, issued May 25, 2004.

Mixtures of abrasives can be used such as mixtures of the various grades of Zeodent® silica abrasives listed above. The total amount of abrasive in dentifrice compositions of the subject invention can range from about 1% to about 75% by weight, or any individual weight percent within the range. Toothpastes may contain from about 10% to about 50% of abrasives, by weight of the composition. Dental solution, mouth spray, mouthwash and non-abrasive gel compositions of the subject invention typically contain little or no abrasive.

Flavoring and Sweetening Agents

Flavoring agents may also be added to the inventive oral care compositions to achieve flavors which are desirable to users of the oral composition. Some examples of suitable flavors include herbals and/or citrus flavors. Such flavoring agents for the herbal and/or citrus flavors may include the essential oils or extracts of these flavors. For example in order to achieve a cinnamon flavor, a suitable flavoring agent may include cinnamon oil. Some suitable examples of herbal flavors include cinnamon which may include flavoring agents such as, e.g. cinnamic aldehyde, methyl cinnamate, cinnamic acid; thyme which may include flavoring agents such as, e.g. thymol, phenol; eucalyptus which may include flavoring agents such as, e.g. eucalyptol; black pepper which may include flavoring agents such as, e.g. b-myrcene, piperitone, piperine; ginger which may include flavoring agents such as, e.g. b-zingerberine, citronellal; peppermint which may include flavoring agents such as, e.g. l-menthol, menthone, menthyl acetate, menthofuran, mint lactone, viridifloral, germacrene d; arvensis which may include flavoring agents such as, e.g. l-menthol, menthone; spearmint which may include flavoring agents such as, e.g. 1-carvone, 1-limonene, 1-carvyl acetate; wintergreen which may include flavoring agents such as, e.g. methyl salicylate; anise which may include flavoring agents such as, e.g. trans anethole; allspice which may include flavoring agents such as, e.g. eugenol, myrcene, alpha terpinene; cassia which may include flavoring agents such as, e.g. cinnamic aldehyde, clove bud which may include flavoring agents such as, e.g. eugenol; coriander which may include flavoring agents such as, e.g. linalool, geraniol, sabinene; bergamot which may include flavoring agents such as, e.g. linaly acetate, pinene. Some suitable examples of citrus flavors may include lemon which may include flavoring agents such as, e.g. citral, decanal, d-limonene, linalyl acetate; orange which may include flavoring agents such as, e.g. octanal, nonanal, d-limonene, ethyl butyrate, acetaldehyde; grapefruit which may include flavoring agents such as, e.g. nookatone; lime which may include flavoring agents such as, e.g. alpha terpineol, hexanal, geranyl acetate; and tangerine which may include flavoring agents such as, e.g. dimethyl anthranylate, thymol, d-limonene.

Other examples of suitable flavors include those found of fruits, dairy products, and/or vanilla. Such flavoring agents for the fruits, dairy products, and/or vanilla flavors may include the natural extracts of these flavors or synthetic analogs thereof. Some suitable examples of fruit flavors include banana which may include flavoring agents such as, e.g. isoamyl acetate, diacetyl, 2-heptanone; apple which may include flavoring agents such as, e.g. ethyl-2-methyl butyrate, 1-butanol, damascenone, trans-2-hexanal; melon which may include flavoring agents such as, e.g. cis-3 hexenyl acetate, 2,6-dimethyl heptenal, methyl 3-nonenoate; peach which may include flavoring agents such as, e.g. gama decalactone, delta-undecalactone, benzaldehyde p-mentha-8-thiol-3-one, isobutyl acetate; pear which may include flavoring agents such as, e.g. ethyl trans-2,cis-4-decadienoate, hexyl acetate, isoamyl acetate; grape which may include flavoring agents such as, e.g. ethyl heptanoate, methyl anthranylate, ethyl maltol; cherry which may include flavoring agents such as, e.g. benzaldehyde, ethyl acetate, ethyl butyrate, cis-3-hexanol; raspberry which may include flavoring agents such as, e.g. cis-3-hexanol, ethyl maltol, beta-ionone; blackberry which may include flavoring agents such as, e.g. ethyl butyrate, alpha-ionone, 1-menthone; blueberry which may include flavoring agents such as, e.g. linalool, geraniol, trans-2-hexanol; strawberry which may include flavoring agents such as, e.g. ethyl methyl phenyl glycidate, cis-3-hexanol, ethyl butyrate; apricot which may include flavoring agents such as, e.g. similar to peach with the addition of geraniol; mango which may include flavoring agents such as, e.g. ethyl acetate, ethyl butyrate, dimethysulfide, furfural; passion fruit which may include flavoring agents such as, e.g. hexyl hexanoate, 2-heptanone, cyclopentenolone; guava which may include flavoring agents such as, e.g. 1-octanol, hexanal, benzaldehyde, acetoin; and pineapple which may include flavoring agents such as, e.g. allyl cyclohexane propionate, ethyl butyrate, 4-hydroxy-2,5-dimethyl-3(2H)-furanone. Some suitable examples of flavors for the dairy and/or vanilla include coffee which may include flavoring agents such as, e.g. furfuryl mercaptan; vanilla which may include flavoring agents such as, e.g. vanillin, ethyl vanillin, heliotropine, dihydrocoumarin; chocolate which may include flavoring agents such as, e.g. isoamyl phenylacetate, p-anisyl acetate, butyric acid, 2,5-dimethylpyrazine butyraldehyde; butterscotch which may include flavoring agents such as, e.g. ethyl vanillin; caramel which may include flavoring agents such as, e.g. butyl lactate, acetanisole; cream which may include flavoring agents such as, e.g. gamma decalactone, acetyl propionyl; and nut which may include flavoring agents such as, e.g. 4-methyl-5-vinythiazole.

Other examples suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Any of the flavoring agents mentioned above may be utilized to create any suitable combination of flavors, e.g. orange—cherry, strawberry banana, vanilla—coffee, strawberry—cream or the like.

Flavoring agents are generally used in the compositions at levels of from about 0.001% to about 5%, by weight of the composition, or any individual number within the range. In some embodiments, the oral care composition may contain about 0.001% by weight to about 5% by weight of a flavoring and/or sweetening agent, or any individual number within the range. In some embodiments, the concentration of the additional flavoring agent/sweetening agent can be greater than about 0.001% by weight, greater than about 0.003%, greater than about 0.005% by weight, greater than about 0.007% by weight, greater than about 0.009% by weight, greater than about 0.01% by weight, greater than about 0.02% by weight, greater than about 0.03% by weight, greater than about 0.04% by weight, greater than about 0.05% by weight, greater than about 0.06% by weight, greater than about 0.07% by weight, greater than about 0.08% by weight, greater than about 0.09% by weight, greater than about 0.1% by weight, greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 1.5% by weight, greater than about 2% by weight, greater than about 2.5% by weight, greater than about 3% by weight, greater than about 3.5% by weight, greater than about 4% by weight, greater than about 4.5% by weight and/or less than about 5% by weight, less than about 4.5% by weight, less than about 4% by weight, less than about 3.5% by weight, less than about 3% by weight, less than about 2.5% by weight, less than about 2% by weight, less than about 1.5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.09% by weight, less than about 0.08% by weight, less than about 0.07% by weight, less than about 0.06% by weight, less than about 0.05% by weight, less than about 0.04% by weight, less than about 0.03% by weight, less than about 0.02% by weight, or less than about 0.01% by weight.

Examples of sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. In some embodiments, a composition may contain from about 0.1% to about 10% of these agents or from about 0.1% to about 1%, by weight of the composition.

Coolants, Salivating Agents, Warming Agents and Numbing Agents

Coolants, salivating agents, warming agents, and numbing agents can be used as optional ingredients in the inventive oral care compositions. In some embodiments, these agents can be present in the compositions at a level of from about 0.001% to about 10% or from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Some examples of suitable salivating agents of the present invention include Jambu® manufactured by Takasago. Examples of warming agents are capsicum and nicotinate esters, such as benzyl nicotinate. Suitable numbing agents include benzocaine, lidocaine, clove bud oil, and ethanol.

In some embodiments, the flavoring agent, coolants, salivating agents, warming agents, and/or numbing agents may be a fluorophore.

Opacifying Agents

The inventive oral care compositions may further comprise an opacifying agent. Any suitable opacifying agent known in the art may be used. Some examples of suitable opacifying agents include titanium dioxide, mica, mica coated titanium dioxide, polyethylene, polypropylene, polyester particulates, combinations thereof, and the like. In some embodiments, the opacifying agent may generally comprise from about 0.001% to about 20% by weight of the dentifrice compositions, or any individual number within the range. In some embodiments, the concentration of the opacifying agent can be greater than about 0.001% by weight, greater than about 0.002% by weight, greater than about 0.003% by weight, greater than about 0.004% by weight, greater than about 0.005% by weight, greater than about 0.006% by weight, greater than about 0.007% by weight, greater than about 0.008% by weight, greater than about 0.009% by weight, greater than about 0.01% by weight, greater than about 0.02% by weight, greater than about 0.03% by weight, greater than about 0.04% by weight, greater than about 0.05% by weight, greater than about 0.06% by weight, greater than about 0.07% by weight, greater than about 0.08% by weight, greater than about 0.09% by weight, greater than about 0.1% by weight, greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, greater than about 10% by weight, greater than about 11% by weight, greater than about 12% by weight, greater than about 13% by weight, greater than about 14% by weight, greater than about 15% by weight, greater than about 16% by weight, greater than about 17% by weight, greater than about 18% by weight, greater than about 19% by weight, and/or less than about 20% by weight, less than about 19% by weight, less than about 18% by weight, less than about 17% by weight, less than about 16% by weight, less than about 15% by weight, less than about 14% by weight, less than about 13% by weight, less than about 12% by weight, less than about 11% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.09% by weight, less than about 0.08% by weight, less than about 0.07% by weight, less than about 0.06% by weight, less than about 0.05% by weight, less than about 0.04% by weight, less than about 0.03% by weight, less than about 0.02% by weight, less than about 0.01% by weight, less than about 0.009% by weight, less than about 0.008% by weight, less than about 0.007% by weight, less than about 0.006% by weight, less than about 0.005% by weight, less than about 0.004% by weight, less than about 0.003% by weight, or less than about 0.002% by weight.

Desensitizing Agents

Another optional ingredient that can be included in the inventive oral care compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Other Active Agents

The inventive oral care compositions may optionally include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent.

The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey.

Other antimicrobials such as copper salts, zinc salts and stannous salts may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific examples of antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from about 0.01% to about 5.0%, by weight of the dentifrice composition.

Surfactants

The inventive oral care compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Examples of other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. In some embodiments, the oral composition may comprise an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, or from about 0.5% to about 2% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants only with this limitation in mind.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Thickening Agents

In preparing toothpaste or gels, thickening agents may be added to provide a desirable consistency to the composition, to provide desirable active release characteristics upon use, to provide shelf stability, and to provide stability of the composition, etc. Some examples of suitable thickening agents include one or a combination of carboxyvinyl polymers, carrageenan, hydroxyethyl cellulose (HEC), natural and synthetic clays (e.g., Veegum and laponite) and water soluble salts of cellulose ethers such as sodium carboxymethylcellulose (CMC) and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Some examples of suitable carboxyvinyl polymers useful as thickening or gelling agents include carbomers which are homopolymers of acrylic acid crosslinked with an alkyl ether of pentaerythritol or an alkyl ether of sucrose. Carbomers are commercially available from B.F. Goodrich as the Carbopol® series, including Carbopol 934, 940, 941, 956, and mixtures thereof.

Copolymers of lactide and glycolide monomers, the copolymer having a number average molecular weight in the range of from about 1,000 to about 120,000, are useful for delivery of actives into the periodontal pockets or around the periodontal pockets as a "subgingival gel carrier." These polymers are described in U.S. Pat. Nos. 5,198,220, and 5,242,910, issued Mar. 30, 1993 and Sep. 7, 1993, respectively both to Damani, and U.S. Pat. No. 4,443,430, issued Apr. 17, 1984 to Mattei.

In some embodiments, thickening agents are typically present in an amount from about 0.1% by weight to about 15% by weight, or any individual number within the range. In some embodiments, the thickening agents may be present in an amount which is greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 1.1% by weight, greater than about 1.2% by weight, greater than about 1.3% by weight, greater than about 1.4% by weight, greater than about 1.5% by weight, greater than about 1.6% by weight, greater than about 1.7% by weight, greater than about 1.8% by weight, greater than about 1.9% by weight, greater than about 2% by weight, greater than about 3% by weight, greater than about 4% by weight, and/or less than about 15% by weight, less than about 10% by weight, less than about 5% by weight, less than about 4% by weight, less than about 3.5% by weight, less than about 3% by weight, or less than about 2.5%. In some embodiments, the thickening agents may be present in a range from about 2% to about 10%, from about 4% to about 8%, by weight of the total toothpaste or gel composition. Higher concentrations may be used for chewing gums, lozenges and breath mints, sachets, non-abrasive gels and subgingival gels.

Humectants

Another optional carrier material of the inventive oral care compositions is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, propylene glycol and trimethyl glycine.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Some examples of suitable chelating agents include sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. In some embodiments, the amounts of chelating agent suitable for use in the present invention can be from about 0.1% to about 5%, or any individual number within the range. In some embodiments, the amounts can be from about 0.5% to about 2.5%, and in some embodiments, from about 1% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Miscellaneous Carrier Materials

Water employed in the preparation of commercially suitable oral compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used alkali metal bicarbonate salt. The present composition may contain from about 0.5% to about 30%, preferably from about 0.5% to about 15%, and most preferably from about 0.5% to about 5% of an alkali metal bicarbonate salt.

The pH of the present compositions may be adjusted through the use of buffering agents. Buffering agents, as used herein, refer to agents that can be used to adjust the pH of the compositions to the pH ranges discussed heretofore. Some examples of suitable buffering agents include sodium bicarbonate, monosodium phosphate, trisodium phosphate, sodium hydroxide, sodium carbonate, sodium acid pyrophosphate, citric acid, and sodium citrate. Buffering agents are typically included at a level of from about 0.5% to about 10%, by weight of the present compositions.

Poloxamers may be employed in the present compositions. A poloxamer is classified as a nonionic surfactant and may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF. Suitable poloxamers for this invention are Poloxamer 407 and Pluraflo L4370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the trade name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Phase Structure

Oral care compositions in accordance with the present invention may comprise a water soluble liquid phase and a water insoluble solid phase. In some embodiments, a ratio of the water insoluble solid phase to the water soluble liquid phase can be from about 1:99 to about 3:1, or any individual ratio within the range. In some embodiments, the ratio of water insoluble solid phase to water soluble liquid phase can be greater than about 1:99, greater than about 1:50, greater than about 1:25, greater than about 1:20, greater than about 1:15, greater than about 1:10, greater than about 1:7, greater than about 1:5, greater than about 1:3, greater than about 1:2, greater than about 1:1, greater than about 2:1, and/or less than about 3:1, less than about 2:1, less than about 1:1, less than about 1:2, less than about 1:3, less than about 1:5, less than about 1:7, less than about 1:10, less than about 1:15, less than about 1:20, less than about 1:25, or less than about 1:50.

In some embodiments, the inventive oral care compositions may comprise from about 25% by weight to about 99% by weight of water soluble liquid phase, or any individual number within the range. In some embodiments, the oral composition may comprise from about 1% by weight to about 75% by weight of water insoluble phase, or any individual number within the range. The water insoluble phase may comprise the abrasives as described above, in some embodiments.

Color and Flavor Effects

As mentioned heretofore, the inventive oral care compositions may comprise colorants and/or flavoring agents. The colorants can be utilized, in some embodiments, to modify the resultant color of the oral composition. Similarly, the flavoring agents, in some embodiments, may be utilized to modify the flavor of the resultant oral composition. Accordingly, embodiments, are contemplated where there is a correlation between the resultant color of the oral composition and the resultant flavor of the resultant composition. For example, where the resultant oral composition color is red, e.g. brick to cherry hue, corresponding flavors may include cinnamon, cherry, strawberry, apple, spice, combinations thereof. As another example, where the resultant oral composition color is orange, e.g. yellow-orange to peach hue, corresponding flavors may include orange, peach, mango, tropical fruits, citrus flavors, citrus mint, etc. As yet another example, where the resultant oral composition color is yellow, e.g. cream to bright yellow hue, corresponding flavors may include banana, lemon, pineapple, vanilla, citrus, tropical, cream, etc. As yet another example, where the resultant color of the oral composition is green, e.g. yellow-green to pine hue, corresponding flavors may include green apple, herbal, lime, spearmint, mint, herbs, fruit, etc. As yet another example, where the resultant color of the oral composition is blue, e.g. aqua to royal hue, corresponding flavors may include wintergreen, peppermint, mint, water, etc. As yet another example, where the resultant color of the oral composition is violet, e.g. navy to magenta hue, corresponding flavors may include blueberry, grape, berry, fruit, etc. As yet another example, where the resultant color of the oral composition is pink, e.g. light pink to fuschia hue, corresponding flavors may include cotton candy, bubblegum, berry, candy, sweet, etc. As yet another example, where the resultant color of the oral composition is grey, e.g. light silver to charcoal or black hue, corresponding flavors may include licorice, anise, spice, etc. As yet another example, where the resultant color of the oral composition is brown, e.g. ivory to sepia, corresponding flavors may include cream, vanilla, caramel, coffee, chocolate, etc.

In the same way, other embodiments are contemplated in which the flavor of the oral composition corresponds with the fluorescing color of the disclosing agent in the compositions.

In some embodiments, the inventive oral composition can include two different flavoring agents, a first flavoring agent designed to generate its characteristic flavor initially on contact with the oral cavity, and a second flavoring agent designed to generate its characteristic flavor after a suitable time delay. This delayed flavor release could occur, for example, because of a slower dissolution rate, or as a result of physical manipulation by a tooth brush, or as a result of contact with a subsequently applied material such as a mouthwash or rinse. Additionally, in some embodiments, the first flavoring agent can be selected to correspond to the color of the oral composition as a whole, or a particular phase of this composition. For example, where the oral composition is a toothpaste, the first flavoring agent and/or the second flavoring agent can be selected to correspond with the fluorescing color emitted by the disclosing agent in the oral composition.

The above variations of color and flavor are also applicable to oral compositions, e.g. dentifrices, comprising stripes or other multiple phases. Any suitable method known in the art can be utilized to impart stripes and/or layers to the dentifrice of the present invention. An example of such a method is disclosed in U.S. Patent Application Ser. No. 60/473,692 filed on Jul. 16, 2003, entitled "Visually distinctive multiple liquid phase compositions".

Packaging Effects

The inventive oral care compositions may be packaged in a variety of different ways. For example, where the oral care composition is a dentifrice, a suitable dispenser may be utilized in which the dentifrice is visible through the dispenser. The dentifrice may have the same or a different color than the dispenser in which it is contained. In some embodiments, the color of the dispenser can be the same or similar to the fluorescing color of the disclosing agent in the composition, both of which can be significantly different from the color of the composition itself. This approach is particularly interesting where the inventive oral care composition includes a flavoring agent corresponding to a color on the package and the fluorescing color of the disclosing agent in the composition.

Additionally, embodiments are contemplated where a consumer may utilize an energy source provided with a brush, for example, to highlight the proper oral composition for use. For example, the packaging of a toothbrush constructed in accordance with the present invention may allow a consumer access to the toothbrush such that an energy source on the toothbrush can be activated. Such packaging is described in U.S. Pat. No. 6,311,837. Additionally, components of the oral composition, e.g. a fluorescing disclosing agent, may be included in the package such that the package or a portion thereof may fluoresce when energy from an energy source is applied thereto. Moreover, the addition of a fluorescing agent to the packaging of an oral composition may not need to be approved by the Federal Food and Drug Administration. Accordingly, more options may exist with regard to the fluorescing agent which can be added to the packaging. Some suitable examples of fluorescing agents which can be added to the packaging are those described heretofore with regard to the disclosing agents. Any suitable fluorescing agent known may be utilized.

Other devices other than a toothbrush are contemplated. For example, the energy source may be located on a store shelf which highlights the aforementioned packages. In some embodiments, store shelves may comprise multiple energy sources which elicit a plurality of responses from a plurality of packages. Embodiments are contemplated where the plurality of responses correspond to a plurality of benefits. For example, blue light may elicit a first response which corresponds to plaque identification, a green light may elicit a response which corresponds to tartar identification, and a red light may elicit a response which corresponds to caries identification. In this manner, the consumer may choose the correct oral composition based on the desired benefit.

Other embodiments are contemplated. For example, in some embodiments, an energy source may be located on a store shelf which allows consumers to fluoresce (highlight) the package which is proper for use. Additionally, embodiments are contemplated where a single energy source may highlight a plurality of packages for varying use. For example, when energy from an energy source is applied to various packaging, a first package may fluoresce a first color, a second package may fluoresce a second color, and a third package may fluoresce a third color. A key may be provided to consumers such that consumers may decipher the color differentiation among the packages. For example, the first color may correspond to an oral composition effective for plaque removal, a second color may correspond to an oral composition effective for teeth whitening, and a third color may correspond to an oral composition effective for antibacterial purposes.

Additionally, embodiments are contemplated where the package itself may include an energy source within the oral care composition itself or within the package but external to the oral care composition.

In some embodiments, the package may be at least partially transparent such that a consumer, seller, distributor, etc., may cause the disclosing agent within the oral composition to fluoresce while the oral composition is within the package and/or on store shelves. In some embodiments, the consumer, seller, distributor, etc. may apply energy to the package such that the package fluoresces. In some embodiments, the consumer may apply energy to the package such that both the package and the oral composition fluoresce.

In some embodiments, the fluorescing color of the package may be similar to the fluorescing color of the disclosing agent within the oral composition. In some embodiments, the fluorescing color of the package may be different from the fluorescing color of the disclosing agent within the oral composition.

For the above embodiments, a separate energy source not associated with a toothbrush may similarly be utilized. For example, a handheld lightpen may comprise the energy source which activates the fluorescing of the packages and/or the oral compositions.

Manufacture

The oral compositions of the present invention can be manufactured in many different ways. In some embodiments, conventional methods of manufacture can be utilized to produce oral compositions described above. Other suitable methods are described below with regard to the manufacture of dentifrices including disclosing agents.

In some embodiments, a dentifrice including a fluorophore such as dibromofluorescein may be produced by providing a premix, an intermediate paste, and the fluorophore. The premix can be provided at a pH greater than or equal to about 9, in some embodiments. In some embodiments, the pH can range from about 7 to about 11 or any individual number within the range. The fluorophore can be dissolved in the premix, and the premix (including the dissolved fluorophore) can be added to the intermediate paste, thereby forming an oral care composition in accordance with the invention.

In some embodiments, a dentifrice including a disclosing agent may be produced by providing the intermediate paste and the fluorophore. In such embodiments, the fluorophore can be added to the intermediate paste. The resultant mixture can be homogenized to produce an oral care composition in accordance with the present invention.

Instruments/Devices

The instruments and devices of the present invention may be utilized separately from the disclosed oral compositions and/or kits of the present invention and/or regimens of the present invention.

In one form, the device may include an energy source to visually enhance a disclosing agent applied to a user's oral cavity, while in another, the device may include bristles for contacting a user's teeth. In yet another form, both the colored bristle and energy source attributes may be combined into a single device. In some embodiments of the first form, the energy source may be contained within a toothbrush. However, any suitable instrument/device may be utilized. Some examples include toothbrushes (both manual and power), wands, dental explorers, flossing devices, water picks, tooth polishers, gum massagers, light pen, and the like. The energy source can be disposed in any suitable location on the device. For example, on a toothbrush, the energy source can be disposed in a head region, in a neck region, and/or in a handle region of the toothbrush.

Additionally, embodiments are contemplated where the energy source is mounted to a fixture within a user's dwelling. For example, the energy source may be mounted in, on, or near a mirror in the bathroom such that the user may can power up the energy source, aim it at his/her oral cavity and look in the mirror in order to view the indicated conditions, e.g. remaining plaque.

In some embodiments, the energy source may include a light source capable of generating light which, in turn, is capable of activating a disclosing agent contained in the oral composition. Normally, such activating light toothbrushes will include a switch enabling the consumer to activate the light source when desired. In addition, such toothbrushes will normally be battery powered, although toothbrushes powered by conventional household and other electrical currents are also contemplated. The brushes may be rechargeable or may be disposable. In embodiments utilizing batteries, the toothbrush may be designed to be rechargeable, disposable, or the toothbrush may be configured to allow the battery to be replaced. Moreover, other embodiments may include brushes which are powered via kinetic energy. For example, some brushes may include a generator which can provide electrical energy by shaking the brush. The generator may then provide power to a storage element, e.g. battery, capacitor, etc. Alternatively, the generator may provide power directly to the energy source.

Some examples of toothbrushes including light sources are disclosed in U.S. Application Publication No. 2005/0053895; 2005/0050658; 2005/0053896; 2005/0050659; 2005/0053898, and WO 2004/030891. Any other toothbrush design which provides a light source capable of generating light at the desired wavelength can also be used. Some examples of other suitable toothbrushes include those described in U.S. Patent Application Publication No. 2005/0108838.

Toothbrushes capable of generating light for activation of the disclosing agent can be either manual or motorized. Some suitable examples of manual toothbrushes to which a light source may be added include those manufactured by Oral-B® and sold under the brand names Indicator®, Stages®, Advantage®, and Cross Action®. Other suitable manual toothbrushes to which a light source may be added are described in U.S. Pat. Nos. 4,802,255; 5,742,972; U.S. Design Pat. Nos. D347,736; and D358,486.

Such toothbrushes can also be motorized, i.e., provided with motor-actuated moving parts to facilitate or improve the brushing action being provided. Examples of suitable motorized toothbrushes include those manufactured by Oral-B® under the brand names Triumph™, Professional Care™, Sonic Complete™, Vitality™, Advance Power, Cross Action® Power, and Pulsar™. These toothbrushes can be readily adapted to use in this invention by adding a suitable energy source thereto such as, for example, by the approaches described in the above-noted U.S. Application Publication No. 2005/0053895; 2005/0050658; 2005/0053896; 2005/0050659; 2005/0053898, and WO 2004/030891. Examples of other suitable toothbrushes which can be readily adapted to utilize an energy source include those described in U.S. Pat. Nos. 6,308,367; 5,742,972; and 6,564,416.

As shown in FIG. 1A, a toothbrush 100 constructed in accordance with the present invention may comprise a head region 110, a neck region 112, and a handle region 114. The handle region 114 may comprise a switch section 120 and a cap section 122. The switch section 120 may comprise a switch 130 which may be capable of activating and de-activating an energy source 150. The switch 130 may comprise an on button 130A and an off button 130B. Alternatively, the switch 130 may comprise a single button which is depressed to activate energy source 150 and subsequently pressed to de-activate the energy source 150. Additionally, in some embodiments, the pressure by the user on the handle of the toothbrush 100 during use may activate the energy source 150 while the release of pressure by the user may de-activate the energy source 150.

The cap section 122 may engage the switch section 120 by any suitable means. For example, the cap section 122 may threadingly engage the switch section 120. This type of engagement may be beneficial where access to an energy store, e.g. a battery, located within the handle region 114 is needed. As another example, the cap section 122 may engage the switch section 120 by a snap fit. As yet another example, the cap section 122 may be welded or adhered to the switch section 120 such that the cap section 122 cannot be separated from the switch section 120 without cutting and/or breaking a portion of the cap section 122 and/or the switch section 120.

The handle region 114 may be constructed by any suitable process. For example, the handle region 114 may be injection molded in one piece utilizing one material. Alternatively, the handle may be injection molded utilizing two separate materials. For example, the electrical function unit or a portion thereof, may be disposed in a first material portion. A second material portion may then be overmolded the first material portion. In some embodiments, the second material may be softer than the first material. For example, the second material may comprise an elastomer while the first material comprises a polyethylene (PE), polypropylene (PP), polyethyleneterapthalate (PET), acrylonitrile-butadiene-styrene (ABS), styrene-acrylonitrile (SAN). Some examples of suitable elastomers include TPE, TPU, rubber, silicone, or the like.

The neck region 112 and the head region 110 may be constructed as an integral piece or may be constructed from several discrete pieces. As shown in FIG. 1A, the neck region 112 is joined to the handle region 114. The neck region 112 may be joined to the handle region 114 by any suitable means. For example, the neck region 112 may be welded to the handle region 114. As another example, the neck region 112 may be adhesively joined to the handle region 114. As yet another example, the neck region 112 may be snap fitted to the handle region 114. As yet another example, the neck region 112 may threadingly engage the handle region 114. Any suitable means for joining the neck region 112 to the handle region 114 may be utilized.

Figure 1B:
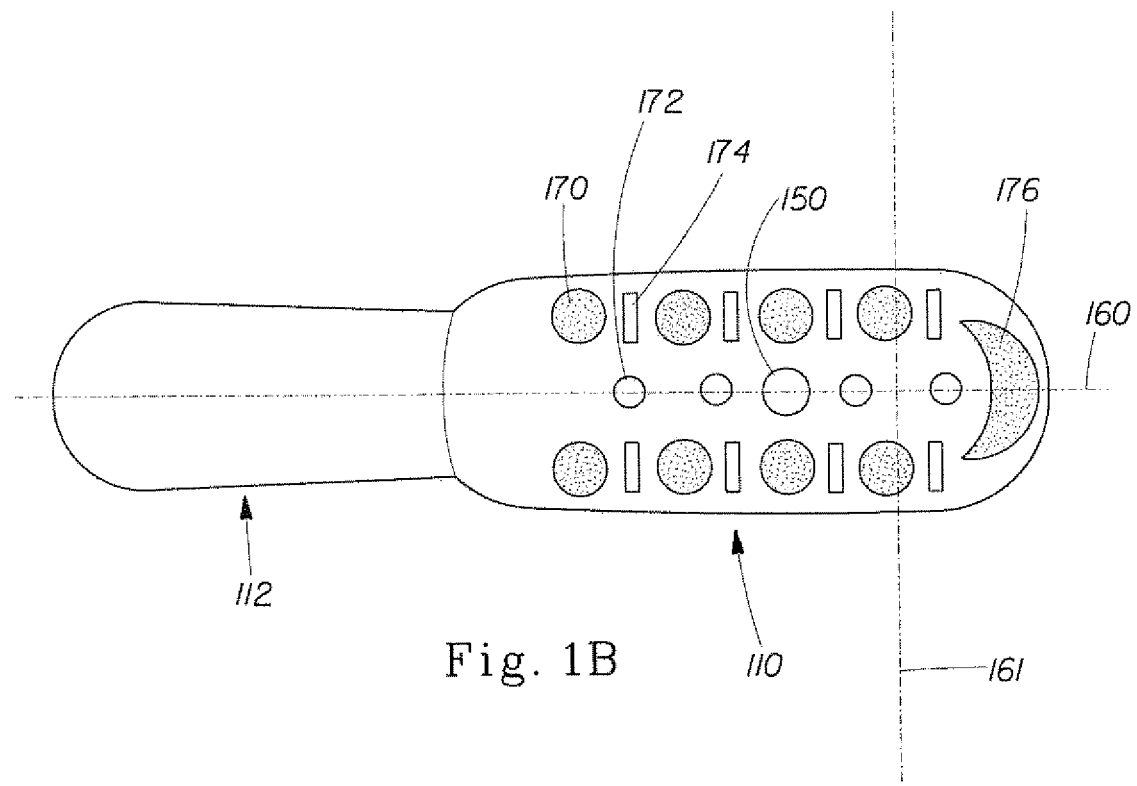
FIG. 1B is a close up plan view showing a head region and a neck region of the toothbrush of FIG. 1A.

The head region 110 has a longitudinal axis 160 and a lateral axis 161 which is generally perpendicular to the longitudinal axis 160 and generally in the same plane as the longitudinal axis 160. A transverse axis (not shown) is generally perpendicular to the longitudinal axis 160 and the lateral axis 161 and also in a plane which is perpendicular to the plane of the longitudinal axis 160 and the lateral axis 161. Additionally, as shown in FIG. 1B, head region 110 comprises a plurality of bristle tufts, e.g. 170, 172, 176, and may further comprise at least one non-bristle element 174, e.g. fins. The bristle tufts 170, 172, 176, may be arranged in any suitable manner. Some examples of suitable configurations/arrangements are described in U.S. Pat. Nos. 5,836,769; 6,564,416; 6,308,367; 6,108,851; 6,058,541; and 5,396,678.

The toothbrush 100 can include any suitable type of bristles. For example, the toothbrush may include textured bristles, e.g., single and multicomponent bristles (e.g., bristles formed by coextruding different polymers), crimped bristles, gum massaging bristles, bristles of varying configurations (e.g., bristles having multiple lumens), and combinations thereof.

Additionally, as shown, the toothbrush 100 (shown in FIG. 1A) may comprise an energy source 150. As shown, in some embodiments, the energy source may be disposed in the head region 110 of the toothbrush (shown in FIG. 1A). However, as previously, stated the energy source 150 may be disposed in any suitable location.

Figure 2:
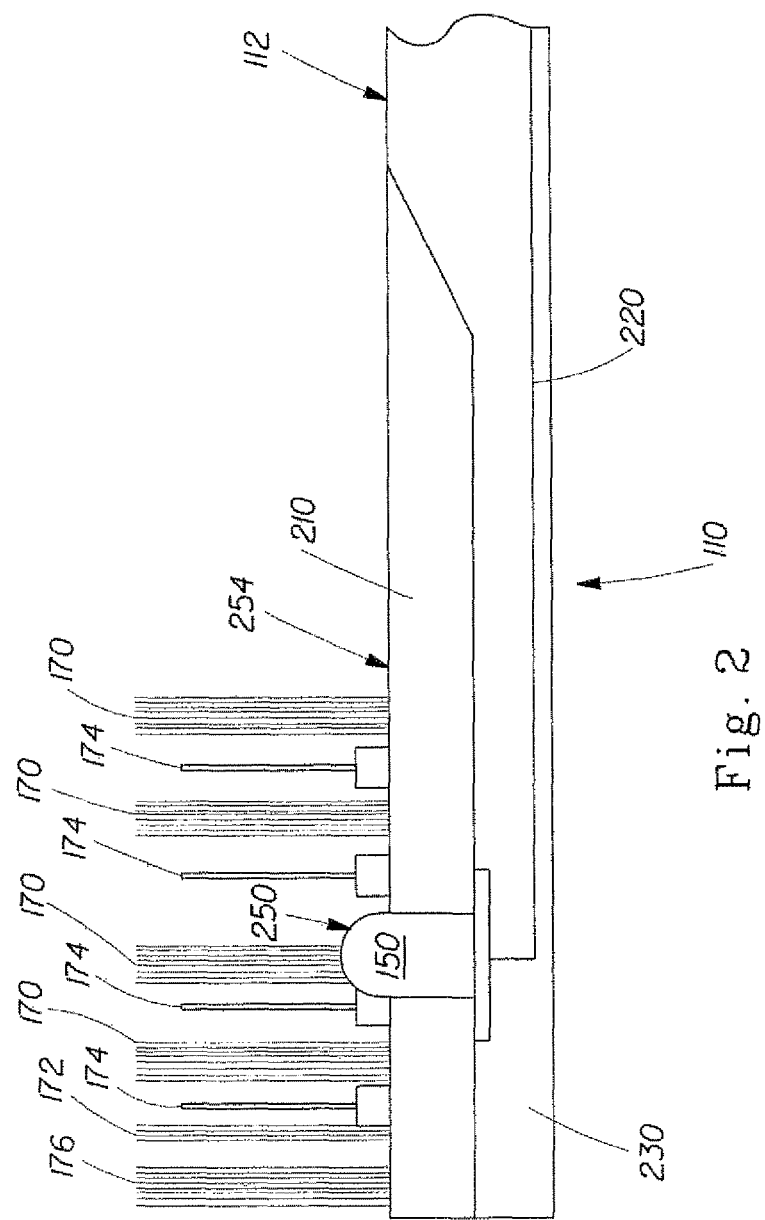
FIG. 2 is a partial cross sectional view showing an embodiment of the head region and neck region of FIG. 1B.

As shown in FIG. 2, the energy source 150, or a portion thereof, may extend above a bristle-facing surface 254. Additionally, as shown, the energy source 150 may comprise a convex outer surface 250, in some embodiments. The convex outer surface 250 may reduce the likelihood of the collection of dentifrice on the outer surface 250 of the energy source 150. Alternatively, the energy source 150 may comprise a flat outer surface which is coplanar with, subjacent to, or superjacent to the bristle-facing surface 254. Although embodiments are shown where the energy source 150 faces toward the bristle-facing surface 254, embodiments are contemplated where the energy source 150 faces (emits energy from) the backside of the head region 110.

As shown, electrical connections 220 may conduct energy from an energy store to the energy source 150. The electrical connections 220 may include wiring in some embodiments. Other suitable examples of electrical connections 220 include those described in U.S. Patent Application Publication No. 2004/0060138.

Additionally, in some embodiments, head region 110 of the toothbrush 100 (shown in FIG. 1A) may comprise discrete components. For example, as shown, the head region 110 may comprise a carrier plate 210 and a base plate 230, in some embodiments. As shown, the carrier plate 210 may be a discrete portion of the head region 110 which is attached to the base plate 230 by any suitable means known in the art. For example, the carrier plate 210 may be adhesively joined to the base plate 230, welded to the base plate 230, and/or snap fitted to the base plate 230.

Figure 3A:
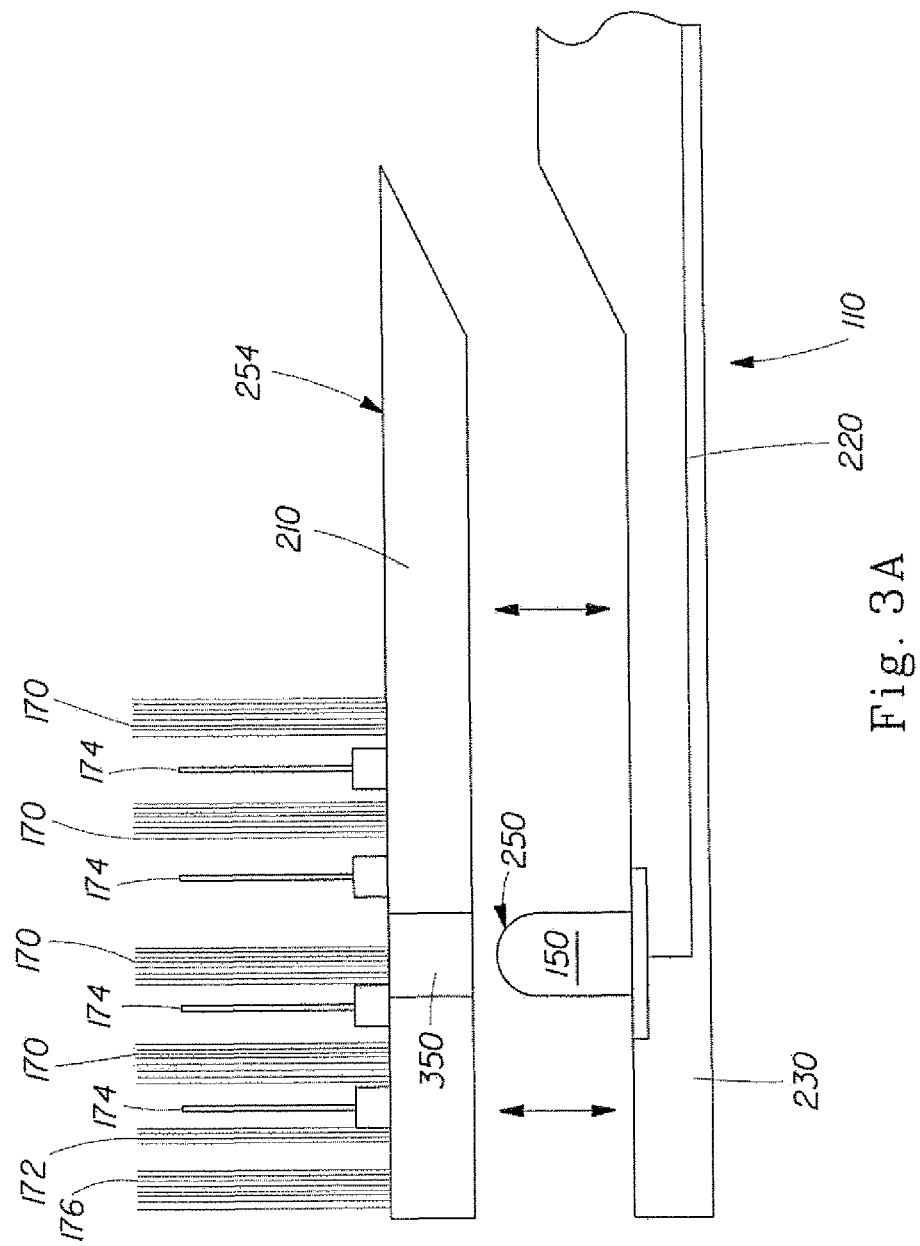
FIG. 3A is an exploded partial cross sectional view showing an embodiment of the head region and neck region of FIG. 2.

As shown in FIG. 3A, the bristles 170, 172, and/or 176, may be attached to the carrier plate 210. In contrast, the energy source 150 may be attached to the base plate 230. The carrier plate 210 may comprise an opening 350 for receiving the energy source 150.

Figure 3B:
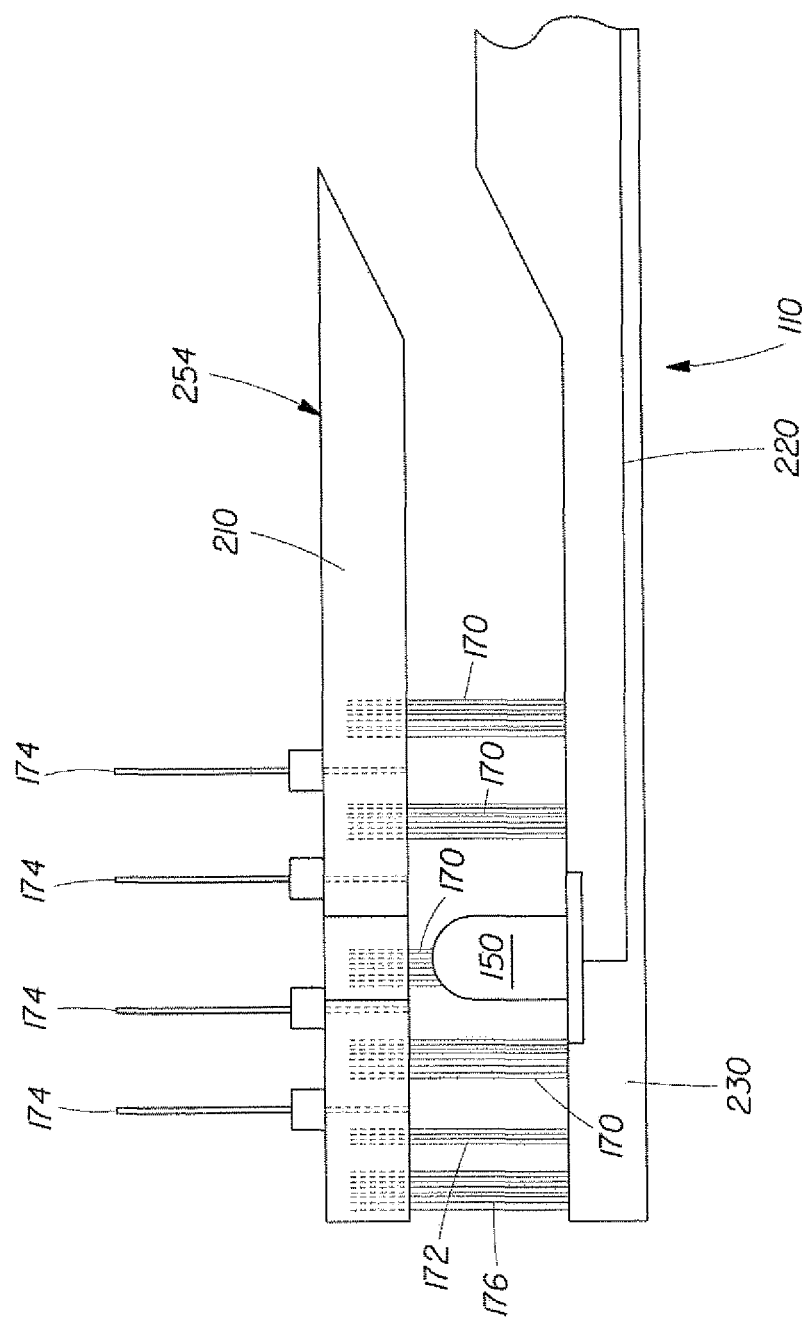
FIG. 3B is an exploded partial cross sectional view showing an embodiment of the head region and neck region of FIG. 2.

As shown in FIG. 3B, the carrier plate 210 may comprise multiple openings which allow the carrier plate 210 to receive the energy source 150 and at least a portion of the bristles 170, at least a portion of the bristles 172, and/or at least a portion of the bristles 176. In some embodiments, the non-bristle elements 174 may similarly be attached to the base plate 230 while the carrier plate 210 comprises opening to receive the non-bristle elements 174 therethrough.

Figure 4A:
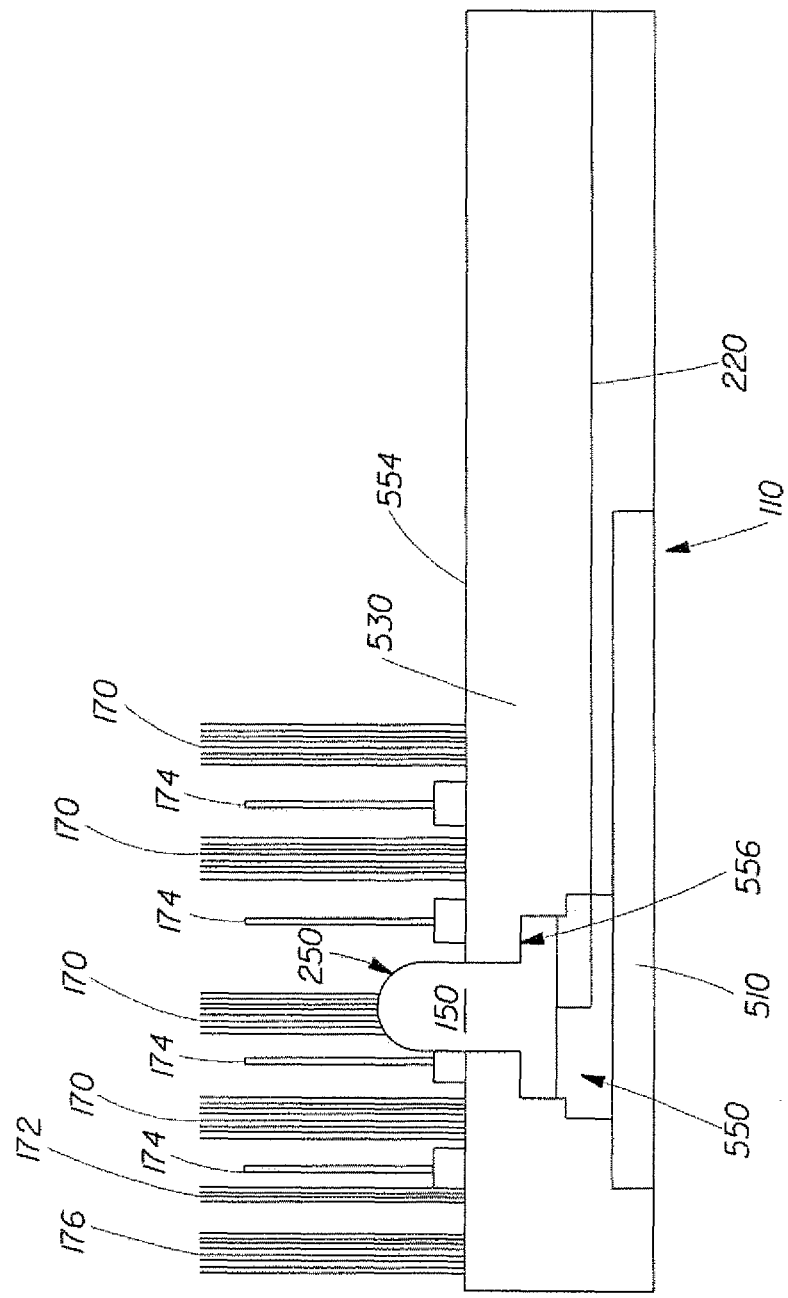
FIG. 4A is a partial cross sectional view showing another embodiment of a head and neck region of a toothbrush constructed in accordance with the present invention.
Figure 4B:
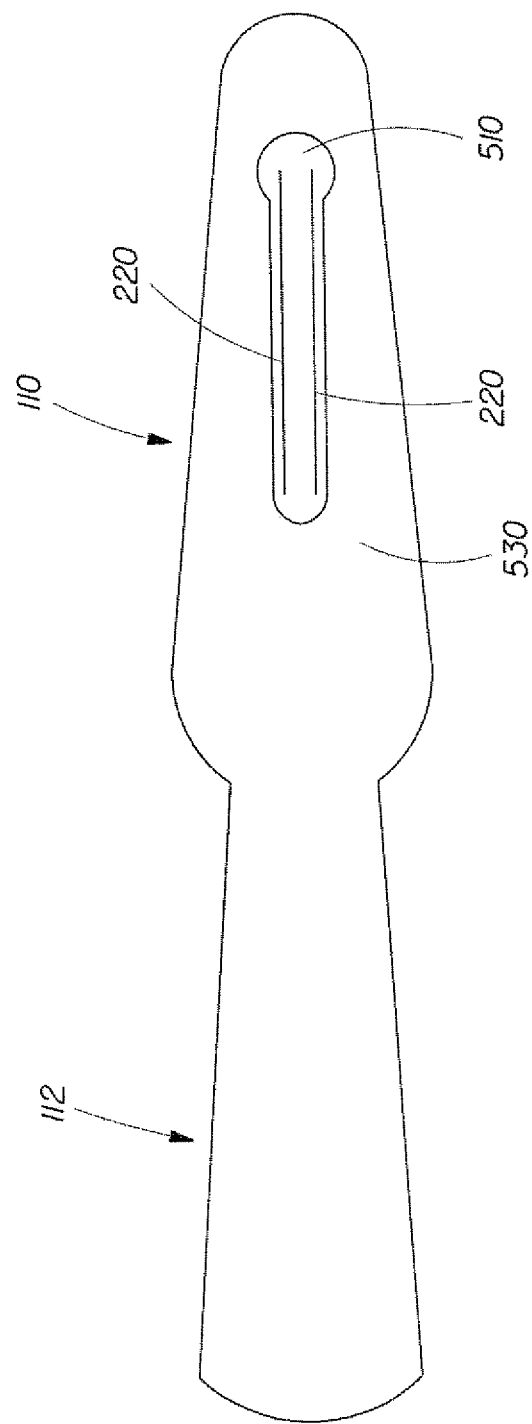
FIG. 4B is a close up plan view showing the head region and the neck region of FIG. 4A.

As shown in FIGS. 4A and 4B, in some embodiments, the head region 110 of the toothbrush 100 (shown in FIG. 1A) may comprise a bristle carrier 530 and a cover plate 510. As shown in FIG. 4A, the bristles 170, 172, and 176, may be attached to the bristle carrier 530 and extend outward from a bristle-facing surface 554 of the bristle carrier 530. The bristle carrier 530 may further comprise an opening 550 therein which allows the energy source 150 to be attached to the bristle carrier 530 on a cover plate-facing surface 556.

The energy source 150 may be attached to the bristle carrier 530 by any suitable means. For example, the energy source 150 may be snap fitted to the bristle carrier 530, adhesively joined to the bristle carrier 530, welded to the bristle carrier 530, or combinations thereof. Additionally, the bristle carrier 530 may be injection overmolded the energy source 150 thereby at least partially encapsulating the energy source 150. The process of injection molding energy sources is described further in U.S. Patent Application No. 2004/0060138.

As shown in FIGS. 4A and 4B, in order to reduce the likelihood that moisture will enter the opening 550, the cover plate 510 may be attached to the bristle carrier 530 thereby enclosing the energy source 150 within the head region 110 of the toothbrush 100 (shown in FIG. 1A). The cover plate 510 may be attached to the bristle carrier 530 by any suitable means. For example, the cover plate 530 may be snap fitted to the bristle carrier 530, adhesively joined to the bristle carrier 530, welded to the bristle carrier 530, or combinations thereof. Additionally, the cover plate 510 may be injection molded into the bristle carrier 530 thereby at least partially encapsulating the energy source 150 within the head region 110.

In a specific embodiment, the energy source 150 may comprise a light source. A wide variety of light-emitting elements may be used with the present invention. For example, the light-emitting elements can be a small, low power consumption, light emitting diode (LED) such as those commercially available under the designation Luxeon™ manufactured by Lumileds Lighting, LLC of San Jose Calif. Other commercially available light-emitting elements include those from American Opto Plus LED Corp. The LED can operate from a relatively low voltage DC power supply, such as greater than about 0.1 volts to about 9 volts. In some embodiments, the LED may operate from a voltage of greater than about 0.1 volts, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6.0, 6.5, 7, 7.5, 8, 8.5, and/or less than about 9, 8.5, 8, 7.5, 7, 6.5, 6, 5.5, 5, 4.5, 4, 3.5, 3, 2.5, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1 volts. The light emitting element may have a diameter of greater than about 0.5, 1, 2, 3, 4, 5, 6, 7, 8, 10, 15, 20 mm and/or less than about 20, 15, 10, 8, 7, 6, 5, 4, 3, 2, or 1 mm.

Additionally, suitable energy sources may emit a wide variety of energy intensities. Any suitable intensity may be utilized. There are several parameters which may be utilized to identify the intensity, flux density, etc. of the energy emission from the LED. For example, Flux Density at a Representative Tooth Surface (FDRT), Percent Total Luminous Flux Within a Solid Angle, Half Angle and/or Viewing Angle, Emission Temperature, and Power Dissipation, can be measured in accordance with the procedure described in U.S. Patent Application Publication No. 2005/0053895.

In general, the power density of the LED will decrease as one moves farther away from the LED. The power intensity may be determined for any distance via sine, cosine, tangent, and/or Pythagorean theorem in conjunction with the light angle of the LED. As shown in FIG. 6, the light angle 610 of the LED 600 is the angle at which light is emitted from the LED. The light angle 610 of the LED can range from about 0 degrees to about 180 degrees, or any individual angle within this range. In some embodiments, the light angle 610 may be greater than about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 130, 140, 150, 160, 170 degrees and/or less than about 180, 170, 160, 150, 140, 130, 120, 110, 100, 90, 85, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 degrees. The light angle 610 is generally obtainable via the manufacturer's specification on the LED.

In some embodiments, the LED may have an FDRT of at least about 0.1 to about 300 mW/cm$^2$. In some embodiments, the FDRT may be greater than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 12, 14, 16, 18, 20, 30, 40, 50, 60, 70, 80, 90, 100, 110, 120, 130, 140, 150, 160, 170, 180, 190, 200, 210, 220, 230, 240, 250, 260, 270, 280, 290 mW/cm$^2$ and/or less than about 300, 290, 280, 270, 260, 250, 240, 230, 220, 210, 200, 190, 180, 170, 160, 150, 140, 130, 120, 110, 100, 90, 80 70, 60, 50, 40, 30, 20, 18, 16, 14, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, or 0.2 mW/cm$^2$.

Relationship Between the Energy Source and the Oral Composition

Figure 5:
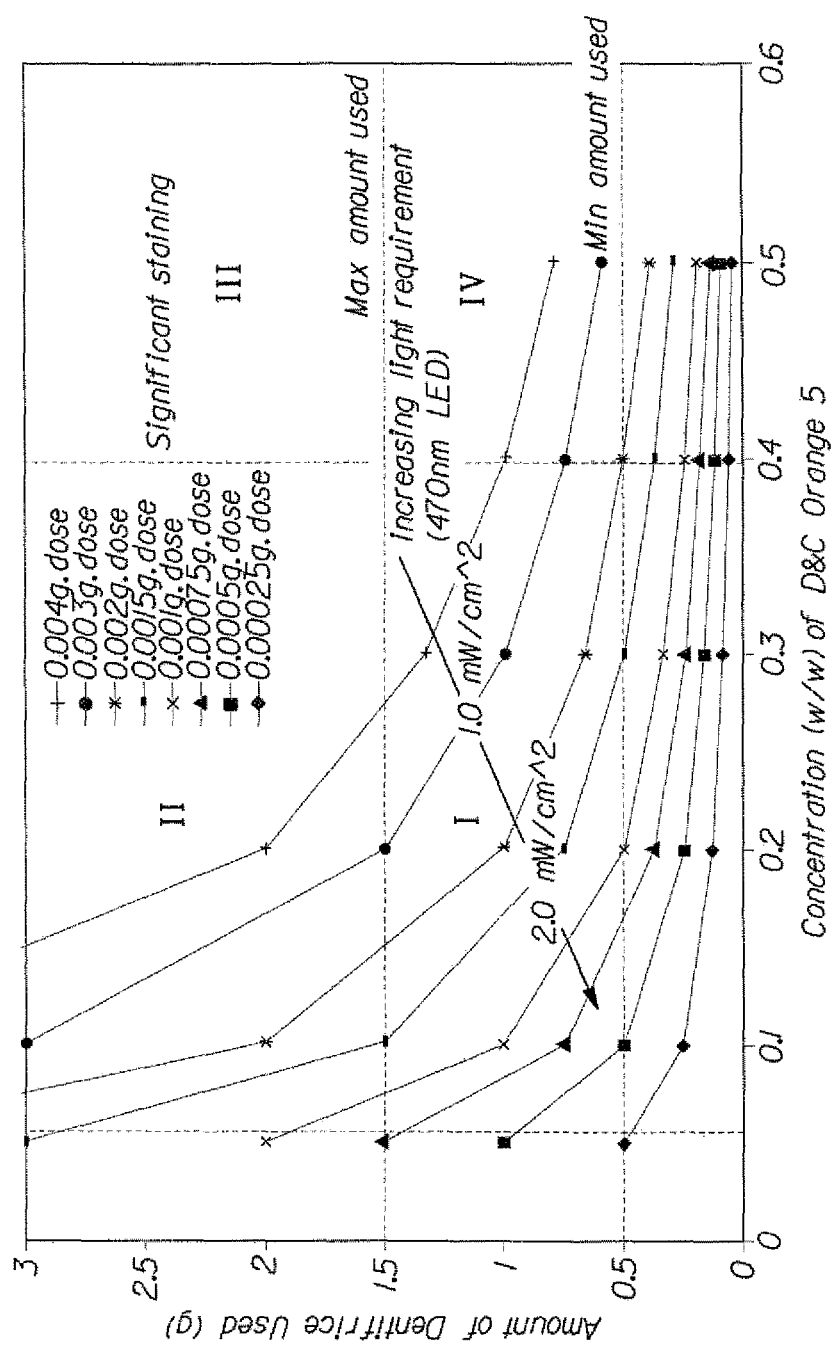
FIG. 5 is a graph showing a correlation between dosage, concentration of disclosing agent, intensity of energy source, and amount of dentifrice used.

As shown in FIG. 5, a relationship between the intensity of the energy from the energy source, the dose, the concentration of the disclosing agent, and the amount of dentifrice used are correlated. The graph of FIG. 5 shows that as the concentration and/or the dosage of the disclosing agent decreases, the intensity of the energy source may be required to provide a contrast between the reflected/emitted energy from the oral cavity and the reflected/emitted energy from the disclosing agent increases.

Additionally, as shown in FIG. 5, concentrations of a disclosing agent of greater than about 0.4 weight percent and an amount of dentifrice used of greater than about 1.5 grams may cause significant staining. Also, note that while FIG. 5 pertains to a dentifrice, a similar relationship exists regardless of the oral composition utilized. For example, as the concentration and/or the dosage of the disclosing agent decreases, the intensity of the energy emitted from the energy source may need to be increased in order to provide a visual contrast between the disclosing agent and the remainder of the oral cavity. Moreover, while FIG. 5 specifically shows D&C Orange 5 as the disclosing agent, a similar relationship also exists with regard to other disclosing agents.

Figure 7A:
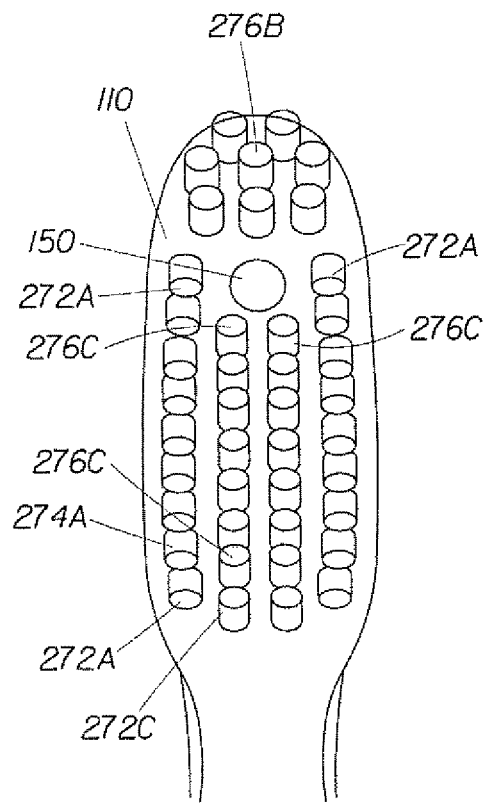
FIG. 7A is a plan view of a toothbrush head according to another embodiment of the present invention.
Figure 7B:
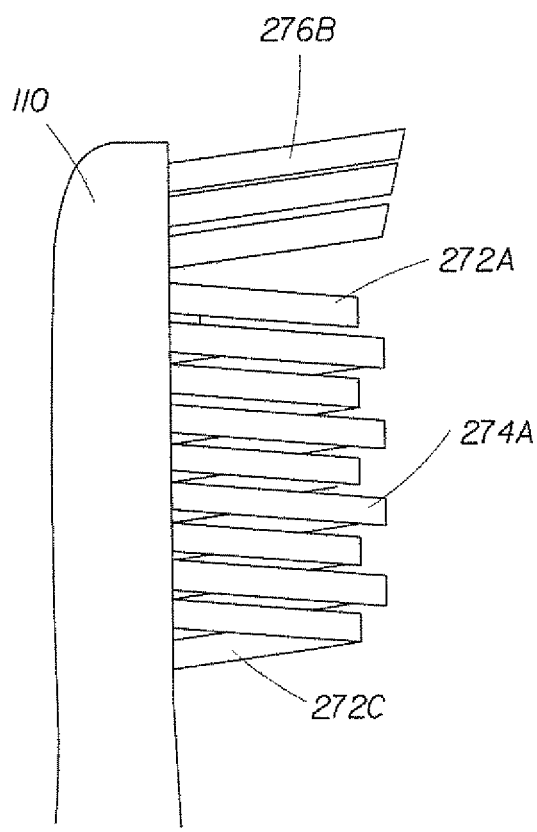
FIG. 7B is a side view of the toothbrush head of FIG. 7A.

Referring next to FIGS. 7A and 7B, an embodiment of a toothbrush head 110 that can lessen the extent of bristle staining associated with the use of a disclosing agent is shown. As with the embodiment depicted in FIG. 1A, toothbrush head 110 includes a plurality of bristles 272, 274 and 276, as well as an energy source 150. It will be appreciated by those skilled in the art that toothbrush head 110 may also be configured without the energy source, and that either configuration is contemplated to be within the scope of the present invention. As concentrations of certain disclosing agents in dentifrice go up (where FIG. 5 shows a particular example using dibromofluorescein (D&C Orange No. 5)), the likelihood of bristle staining also goes up. By having at least some of the bristles colored substantially similarly to the color of the disclosing agent, the appearance of brush staining is reduced. In one form, the bristles may be made up of a few different colors, and arranged in a repeating color pattern. For example, in cases where the disclosing agent is dibromofluorescein, a portion of the outer row bristles 272A may be colored orange, which alternate in color with other outer row bristles 274A, which may be a darker color (for example, blue). Likewise, bristles 276B, disposed at the tip of toothbrush head 110, may be formed of a different color (for example, a generally clear or white color). Inner row bristles 272C may also be made orange-colored, and made to alternate with inner row bristles 276C, which could be of a similar color to tip bristles 276B. Referring with particularity to FIG. 7B, the outer row bristles 272A and 274A can be made of staggered lengths such that the orange-colored outer row bristles 272A are shorter than their alternating counterparts 174A. Also as shown, the entire inner row 272C and 276C, as well as outer row 272A can be made of comparable length.

Additionally, in some embodiments, the bristles most adjacent to the energy source 150, e.g. 276B, 272A, and/or 276C, may be disposed in the head of the toothbrush at an angle. For example, as shown, the bristles 276B may be generally disposed at an angle with respect to the head region 110 wherein the bristles 276B are angled away from the handle of the toothbrush. In contrast, the bristles 272A and/or 276C may be angled toward the handle, in some embodiments.

The angles for the bristles 276B, 272A, and/or 276C can be measured with respect to the transverse axis of the head region 110. For example, the angle that the bristles 276B, 272A, and/or 272C make with the transverse axis of the head region 110 can be greater than about 0.5 degrees, greater than about 1 degree, 2 degrees, 3 degrees, 4 degrees, 5, degrees, 6 degrees, 7 degrees, 8 degrees, 9 degrees, 10 degrees, 11 degrees, 12 degrees, 13 degrees, 14 degrees, 15 degrees, 17 degrees 18 degrees, 19 degrees, 20 degrees, 25 degrees 30 degrees, 35 degrees and/or less than about 35 degrees, 30 degrees, 25 degrees, 20 degrees, 19 degrees, 18 degrees, 17 degrees, 16 degrees, 15 degrees, 14 degrees, 13 degrees, 12 degrees, 11 degrees, 10 degrees, 9 degrees, 8 degrees, 7 degrees, 6 degrees, 5 degrees, 4 degrees, 3 degrees, 2 degrees, or 1 degree.

The angling of bristles away from the energy source 150 may be beneficial after some period of use of the toothbrush. For example, over a period of time, after substantial use, the bristle filaments of a toothbrush often have a tendency to become set in a curled or bent position. Where the energy source 150 is an LED, for example, curled and/or bent bristle filaments could block the light path of the LED thereby reducing the efficacy of the LED. As such, angling the bristles away from the LED can allow for some curling or bending of the bristle filaments without reducing the efficacy of the LED.

Kits

Heretofore, oral compositions of the present invention and devices of the present invention for activating such oral compositions have been described. However, the present invention also contemplates kits of the above oral compositions and devices. For example, in some embodiments, a system of the present invention may comprise an oral composition comprising a disclosing agent capable of indicating oral conditions, e.g. plaque and an energy source for activating this disclosing agent. In some embodiments, the disclosing agent may not be visually perceptible without the application of energy from the energy source.

In some embodiments, a kit of the present invention may comprise a dispenser for the oral composition, the toothbrush including an energy source for activating this disclosing agent and optional directions for their use, these items typically being combined in a single package. The kit may comprise one or more oral care compositions. Some suitable examples of oral care compositions include toothpastes, dentifrices, tooth gels, subgingival gels, foams, mouthrinses, denture products, mouthsprays, lozenges, chewable tablets or chewing gums and strips or films for direct application or attachment to oral surfaces including any hard or soft oral tissues.

To use this system, the consumer applies the oral composition to the oral cavity. For example, where the oral composition is a dentifrice, the consumer may apply the disclosing agent to his/her teeth simply by brushing. As another example, where the oral composition is a mouthrinse, the consumer may apply the disclosing agent to the oral cavity simply by swishing the mouthrinse within the oral cavity. Where the oral composition is a mouthrinse, the application of the disclosing agent to the oral cavity can occur before or after the consumer brushes his/her teeth. The application of the disclosing agent within the oral cavity may take from a few seconds to a few minutes and may vary depending on the type and concentration of the particular disclosing agent used. Additionally, the application of the disclosing agent may also depend on the medium utilized to deliver the disclosing agent. For example, the application of the disclosing agent in a dentifrice via brushing may take longer than the application of a disclosing agent in a mouthrinse via swishing the mouthrinse within the oral cavity.

Where the application of the disclosing agent is via brushing, in some embodiments, brushing may extend from about 5 seconds to about 120 seconds, or any individual number within the range. In some embodiments, the brushing may be greater than about 10 seconds, may be greater than about 20 seconds, may be greater than about 30 second, may be greater than about 40 seconds, may be greater than about 50 seconds, may be greater than about 60 seconds, may be greater than about 70 seconds, may be greater than about 80 seconds, may be greater than about 90 seconds, may be greater than about 100 seconds, may be greater than about 110 seconds and/or may be less than about 120 seconds, may be less than about 110 seconds, may be less than about 100 seconds, may be less than about 90 seconds, may be less than about 80 seconds, may be less than about 70 seconds, may be less than about 60 seconds, may be less than about 50 seconds, may be less than about 40 seconds, may be less than about 30 seconds, or may be less than about 20 seconds.

After the application of the disclosing agent to the oral cavity, the consumer may optionally remove oral compositions, e.g. dentifrices, by rinsing his/her mouth in a customary manner or simply by expectorating. In some embodiments, the person may be instructed not to rinse or spit thereby enabling a higher disclosing agent concentration within the oral cavity. If the person rinses, the person may rinse with water or may rinse with a mouthrinse. Utilization of a mouthrinse which similarly comprises the disclosing agent may be beneficial in ensuring that all of the surfaces within the oral cavity are exposed to the disclosing agent.

Additionally, where the oral composition is applied to the oral cavity through brushing, the user may rinse off the toothbrush. This step may be useful where the energy source is in the head of the toothbrush and faces a bristle field of the brush. In these instances, during the application of the oral composition, the energy source may be covered, at least in part, with spent oral composition prior to the rinsing of the toothbrush. As such, rinsing the toothbrush may reduce the likelihood that the energy intensity from the energy source is reduced by spent dentifrice.

In order to reveal conditions that may be present in the oral cavity, the user or third person may apply the energy source to the oral cavity. In embodiments where the energy source is on the toothbrush, a portion of the toothbrush including the energy source can be inserted into the oral cavity. Upon application of the energy from the energy source, the disclosing agent may fluoresce. As such, the disclosing agent may reveal conditions, e.g. remaining plaque, to the user and/or an observer. While the observer may be able to directly view the fluorescing areas of the oral cavity, the user may have to utilize a mirror in order to view the fluorescing areas of the oral cavity.

One benefit of having an energy source disposed in a toothbrush head such that the energy source emits energy from a bristle-facing surface of the toothbrush head, is that the toothbrush can assist the user in moving soft tissue in order to facilitate viewing. For example, a user may brush with a toothbrush constructed in accordance with the present invention. Additionally, in order to evaluate the brushing done, the user may activate the energy source on the toothbrush without removing the toothbrush from the oral cavity. The back of the toothbrush head may be utilized to move soft tissue such that the energy source is at a distance away from the intended evaluation spot such that viewing the indication is facilitated.

In some embodiments, the distance between the surfaces of the oral cavity and the energy source can be between about 0.1 mm to about 60 cm, or any individual number within the range. In some embodiments, the distance between the energy source and the condition within the oral cavity can be greater than about 0.1 mm, greater than about 0.2 mm, greater than about 0.3 mm, greater than about 0.4 mm, greater than about 0.5 mm, greater than about 0.6 mm, greater than about 0.7 mm, greater than about 0.8 mm, greater than about 0.9 mm, greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, greater than about 10 mm, greater than about 11 mm, greater than about 12 mm, greater than about 13 mm, greater than about 14 mm, greater than about 15 mm, greater than about 16 mm, greater than about 17 mm, greater than about 18 mm, greater than about 19 mm, greater than about 20 mm, greater than about 25 mm, greater than about 30 mm, greater than about 35 mm, greater than about 40 mm, greater than about 45 mm, greater than about 50 mm, greater than about 55 mm, greater than about 60 mm, greater than about 70 mm, greater than about 80 mm, greater than about 90 mm, greater than about 100 mm, greater than about 110 mm, greater than about 120 mm, greater than about 140 mm, greater than about 160 mm, greater than about 180 mm, greater than about 200 mm, greater than about 220 mm, greater than about 240 mm, greater than about 260 mm, greater than about 280 mm, greater than about 300 mm, greater than about 320 mm, greater than about 340 mm, greater than about 360 mm, greater than about 380 mm, greater than about 400 mm, greater than about 420 mm, greater than about 440 mm, greater than about 460 mm, greater than about 480 mm, greater than about 500 mm, greater than about 520 mm, greater than about 540 mm, greater than about 560 mm, greater than about 580 mm and/or less than about 600 mm, less than about 580 mm, less than about 560 mm, less than about 540 mm, less than about 520 mm, less than about 500 mm, less than about 480 mm, less than about 460 mm, less than about 440 mm, less than about 420 mm, less than about 400 mm, less than about 380 mm, less than about 360 mm, less than about 340 mm, less than about 320 mm, less than about 300 mm, less than about 280 mm, less than about 260 mm, less than about 240 mm, less than about 220 mm, less than about 200 mm, less than about 180 mm, less than about 160 mm, less than about 140 mm, less than about 120 mm, less than about 100 mm, less than about 80 mm, less than about 60 mm, less than about 40 mm, less than about 20 mm, less than about 10 mm, less than about 9 mm, less than about 8 mm, less than about 7 mm, less than about 6 mm, less than about 5 mm, less than about 4 mm, less than about 3 mm, less than about 2 mm, less than about 1 mm, less than about 0.9 mm, less than about 0.8 mm, less than about 0.7 mm, less than about 0.6 mm, less than about 0.5 mm, less than about 0.4 mm, less than about 0.3 mm, or less than about 0.2 mm.

As a next step, the user or third person may rebrush or brush (if a rinse was used previously) the areas of the oral cavity which fluoresced in order to remove the remaining plaque or alleviate the indicated condition. In some embodiments, after applying energy to the oral cavity to reveal conditions within the oral cavity, the next step may include brushing, rinsing, flossing, picking, applying anti-plaque agents, or combinations of these. Subsequently, the steps from above may be repeated. Specifically, the user may again rinse their mouth out to remove a portion of the spent dentifrice. Additionally, the user or third person may apply the energy source to the oral cavity to once again view the remaining plaque on the teeth in question. If desired, additional disclosing agent can also be applied to the teeth with optional brushing to supply additional disclosing agent to the oral cavity to possibly highlight the condition more intensely.

Additionally, kits of the present invention may include various teeth cleaning devices which are specifically designed for a particular purpose. For example, where the highlighted areas are mainly interdental, an interdental device may be utilized, e.g. power flosser, floss, toothbrush with an interdental head, e.g Oral-B® End-Tufted Brush. As yet another example, where the highlighted areas are mainly on the gumline or on the gums, a gum cleansing device may be utilized, e.g. Oral-B® Gum Stimulator.

Alternatively, embodiments are contemplated where the kit includes an electric toothbrush base with multiple interchangeable heads. For example, for application of the disclosing agent and normal brushing, a first brushhead may be used for normal brushing. However, where the highlighted areas are mainly interdental and along the gum line, a second brushhead may be utilized, e.g. Oral-B® Power Tip®. As such, embodiments, are contemplated where the kit includes an electric toothbrush having multiple head attachments for performing different functions within the oral cavity.

After rebrushing, any remaining fluorescing areas may be indicative of a secondary or serious dental and/or oral cavity issue. As such, a user may wish to seek the assistance of a dental professional as the next step.

The particular disclosing agent selected for use in the present invention, as well as its concentration, can be selected so that this disclosing agent is not visually perceptible, or at least not easily visually perceptible, outside of the application of energy from an energy source to the disclosing agent. As a result of this approach, significant staining of the oral cavity and other surfaces that may come into contact with the oral composition, which is a common problem with conventional plaque disclosing agents such as those based on large quantities (i.e. >0.01 g) of erythrosine (FD&C Red Dye No. 3), for example, is largely eliminated. This is because the disclosing agent remains not easily visually perceptible under normal use conditions and only becomes more visually perceptible when illuminated at the discretion of the user. At the same time, however, when this disclosing agent is illuminated, it may provide clear visual evidence of the presence of a condition in the oral cavity, e.g., plaque not removed by a brushing operation, due to its emission of visible light desirably at a distinctly different color than the light supplied by the energy source, in some embodiments.

As stated previously, in some embodiments, the disclosing agent can be selected to emit light whose color is significantly different from the color of the oral composition in which it is supplied. For example, where the oral composition is a red color, the fluorescing color of the disclosing agent can be orange. As yet another example, where the oral composition is green in color, the fluorescing color of the disclosing agent can be yellow.

Many variations in the system described above are possible. For example, instead of a toothbrush including the energy source for inducing the disclosing agent to fluoresce, energy can be supplied from a separate energy source. Some suitable examples of separate energy sources may include a flashlight, light wand, dental pick with attached light source, a gum stimulator incorporating an energy source, etc. In this instance, a system could desirably be formed from the combination of the inventive oral compositions as described above together with this separate energy source.

Similarly, instead of using a dentifrice to supply the disclosing agent as described above, other carriers such as mouthwashes, mouth rinses, powders, paint-on gels, strips, films, mouthsprays, lozenges, chewable tablets, chewing gums, denture products and the like can also be used for this purpose. In this instance, a home-care plaque removal system could desirably be formed from the combination of the activating light toothbrush, as described above, together with this other fluorophore-containing carrier.

Although the kits described above can be used separately to great advantage, it can also be combined with other treatments to develop a comprehensive oral care regimen providing still further oral health benefits. For example, using the kits described above can be followed by treatment with an antimicrobial rinse for killing plaque bacteria. Some suitable examples of such antimicrobial rinses are described in U.S. Pat. No. 4,592,488 and U.S. Patent Application Publication No. 2005/0169852 A1. This treatment may be even more effective if the antimicrobial rinse follows treatment with the fluorophore-containing dentifrice or carrier by a suitable elapse of time, e.g., 15 minutes, 30 minutes or even an hour.

Additionally or alternatively, plaque removal using the inventive kits as described above can be followed by or combined with treatment with an a mouthwash or rinse for providing caries protection using various fluoride salts, for example; gingivitis prevention using antimicrobial agents such as triclosan, stannous fluoride, or essential oils for example; or hypersensitivity control through using ingredients such as strontium chloride or potassium nitrate, etc. A single mouthwash or rinse containing some or all of these ingredients, including antimicrobial agents for killing plaque bacteria can also be used.

The regimen may further include the step of flossing, preferably immediately before or immediately after the brushing and optional rinsing steps. Flossing cleans the areas between the teeth, the gum line and other hard to reach areas and makes these areas more accessible for delivery of actives from the dentifrice and optional rinse. Preferably, the floss itself contains an antimicrobial active that is delivered during flossing. The floss may be supplied already containing an antimicrobial or the consumer may impregnate the floss with the antimicrobial dentifrice or mouthwash as part of the regimen.

Further, the regimen may include a disinfecting step using the antimicrobial mouthwash as disinfectant for the toothbrush or interdental device to avoid reintroduction of microbes in the mouth.

For carrying out these regimens, this invention also contemplates modified oral hygiene kits including one or more of additional implements and/or supplies to carrying out the additional step or steps such regimens may include. For example, a modified kit may additionally include an antimicrobial mouthwash, and/or at least one interproximal device and optional instructions for conducting a regimen to achieve optimum benefits. The oral composition in this modified kit may also include an antimicrobial agent for killing plaque bacteria, if desired. Such modified kits and regimens would be particularly useful for consumers having or at risk for development of gingivitis and periodontal disease, for example. It is also contemplated that such modified oral hygiene kits, while including one or more additional implements and/or supplies as indicated above, could also eliminate either the fluorophore-containing oral care compositions or the activating light device of this invention.

Regimens may also be designed for daily, bi-weekly, weekly, monthly, or any other time period. A regimen may be designed for maximum benefit if it is performed at certain times of the day such as at night, in the morning, within a certain time period (for example over four hours), or throughout the day. A weekly regimen may include the use of one or more products that are only used once or twice per week. For example, a whitening product may only be used once a week, another day may be for use of a deep cleaning dentifrice, and another day for use of an intensive product. The intensive product may be a gel, serum or other form that provides extra fluoride, enhanced antimicrobials or any other oral care active ingredient that provides a benefit from use on a less than daily basis.

One step in a regimen may comprise the use of an activator composition. The activator composition may be a rinse or gel or in any other form that delivers the composition to the oral surfaces. The activator composition is intended to enhance the treatment or effect of the subsequent step. For example, an activator rinse may be used pre-brushing to enable better fluoride absorption during brushing with a fluoride dentifrice. An activator gel may be used as a pre-whitening step for better whitening or peroxide absorption.

One embodiment contemplates an intensive night treatment to protect the mouth throughout the night when the mouth is most vulnerable for plaque bacteria to flourish, as evidenced in a common consumer complaint of morning mouth malodor. The regimen includes a rinsing step using an activator rinse followed by application of a treatment product containing ingredients such as whitening agents, antimicrobials, and fluoride. The intensive treatment product preferably will include as carrier for the oral care active(s), a material that is substantive to teeth and other oral surfaces and will thus deposit a coating thereon to facilitate deposition and retention of actives onto the oral surfaces where they can perform their intended function. In addition, the substantive coating provides resistance to soiling, staining and adherence of bacteria and other unwanted deposits. Compositions suitable as intensive treatment products are disclosed for example in U.S. Pat. No. 7,025,950 and U.S. application Ser. No. 10/430,520 published as US 20030211050A1 using anionic functionalized polysiloxanes as substantive agent and in U.S. Pat. Nos. 6,555,094; 6,821,507 and 6,713,049 using polyphosphates.

In some embodiments, one step in a regimen may comprise a booster product. This may be a composition which is put on the toothbrush with a dentifrice. The booster product may include a disclosing agent as discussed herein. The booster product may be a serum, gel, liquid or other form that could be combined with a dentifrice. The booster product may be used occasionally with a brushing step or as specified in a regimen.

In another embodiment, a regimen is designed for balancing and controlling the pH in the oral cavity. The regimen includes the steps of brushing and rinsing with an antimicrobial product. The antimicrobial products may preferably be formulated to provide enhanced buffering capability in the mouth. The steps in the regimens are preferably spaced apart for maximum effectiveness. Preferably, a rinsing step will occur at least 30 minutes after and up to 120 minutes after bushing. The regimen also preferably comprises a rinsing or brushing step after each meal. A kit for a regimen for balancing the pH in the oral cavity may include an antimicrobial dentifrice, an antimicrobial mouthrinse, and a small or travel size antimicrobial dentifrice or mouthrinse for use out of the home.

As described above, the present regimens may include use of interproximal devices such as dental floss. A dental floss suitable for use is disclosed for example, in U.S. Pat. No. 5,518,012 to Dolan et al., which discloses an expanded polytetrafluoroethylene (PTFE) floss that can incorporate anti-microbial agents such as cetyl pyridinium chloride. A dental floss containing a first anti-microbial agent may be used after a rinse also containing the first anti-microbial agent and/or a second anti-microbial agent. For example, a dental floss could contain cetyl pyridinium chloride (CPC) and the rinse could also contain cetyl pyridinium chloride or, alternatively, hydrogen peroxide. A rinse containing high bio-available levels of CPC is marketed by the Procter & Gamble Company as Crest Pro Health™. The rinse and dental floss might be used in the evening in combination with a strip of material containing a peroxide active which might be used in the morning or anytime prior to evening. An example of such as strip of material is disclosed in U.S. Pat. No. 5,891,453 to Sagel et al., which might be used in the morning. Alternatively, the strip of material could contain an anti-microbial or anti-bacterial agent such as disclosed in U.S. Pat. No. 6,096,328 to Sagel et al. In yet another embodiment, the strip of material can contain a tooth whitening agent in combination with one or more an anti-microbial agents, an example of which is disclosed in U.S. Application No. 60/701,778 filed Jul. 22, 2005 entitled Tooth Whitening Products. In yet another embodiment, a rinse and floss containing an antimicrobial agent can be used in the evening in combination with a strip of material containing an anti-microbial agent that can be worn while sleeping, a strip of material that could be suitable for use while sleeping and which could incorporate an antimicrobial agent is disclosed in U.S. Pat. No. 6,649,147 to Ye et al. The foregoing regimens can further be combined, in whole or part, with a toothbrush that can deliver an antimicrobial agent to the oral cavity or which can prevent or reduce the growth of microbials on a toothbrush and thereby reduce or eliminate transmission of microbials from a toothbrush to the oral cavity, examples of which are disclosed in U.S. Pat. Nos. 5,998,431 and 6,009,589. Any of the foregoing products can be combined and packaged as a kit and distributed as a single system of oral care components.

In yet another embodiment, a toothbrush that delivers oxygen or oxygen radicals at or below the gingival tissues can be combined in whole or part with the regimens and products described above. In one example, a vibrating toothbrush can be used to deliver oxygen or oxygen radicals to the gingival tissue. A toothbrush that could be suitable for use is disclosed in U.S. Pat. No. 5,378,153. A toothbrush that delivers a composition comprising an oxygen generating agent, such as a peroxide (e.g., hydrogen peroxide, carbamide peroxide, and calcium peroxide), to the gingival tissue can also be used. Examples are disclosed in U.S. Pat. Nos. 5,476,384 and 6,648,641 of toothbrushes that could dispense and deliver a composition comprising an oxygen generating agent to, or below the gingival tissue.

In one regimen, a rinse or floss comprising an oxygen generating agent might be used in combination with a toothbrush that dispenses or delivers an oxygen generating agent. In another embodiment, a rinse or floss that delivers a first agent to, or below, the gingival tissue might be used in combination with a toothbrush that delivers a second agent that, when combined with the first agent, generates oxygen, oxygen radicals, other radicals, and/or mixtures thereof. Alternatively, the toothbrush might deliver the first agent and the rinse and/or floss might deliver the second agent. The first agent might be provided with an affinity for tartar, plaque, or oral tissues (e.g., soft and/or hard tissues) so that application of the second agent generates oxygen, oxygen radicals, or other radicals at the locations where bacteria and other microbials may be concentrated, including locations at or below the gingival tissue.

In yet another embodiment, the floss might deliver the first agent and the rinse might deliver the second agent. Examples of compositions that can adhere to oral/organic tissues to deliver a first agent are disclosed in U.S. Publication Nos. 2003/0211051 and 2003/0211050. First and second agents that can generate oxygen, oxygen radicals, other radicals, and/or mixtures thereof, directly or indirectly, that might be suitable for use are disclosed for example in U.S. Pat. No. 5,302,375 to Viscio.

Dental Office Applications

In yet another embodiment, the floss might deliver the first agent and the rinse might deliver the second agent. Examples of compositions that can adhere to oral/organic tissues to deliver a first agent are disclosed in U.S. Publication Nos. 2003/0211051 and 2003/0211050. First and second agents that can generate oxygen, oxygen radicals, other radicals, and/or mixtures thereof, directly or indirectly, that might be suitable for use are disclosed for example in U.S. Pat. No. 5,302,375 to Viscio.

The oral compositions, devices, kits, regimens, of the present invention while effective for consumers may similarly be utilized by dental professionals in a dental office or other similar environment. For example, dentifrice created in accordance with the present invention, can be used in the dental office with an activating light toothbrush or with another activating light source designed especially for commercial use. Normally, such a commercial "heavy-duty" activating light source would be powered by standard line current (60 Hz/120V in the U.S.), although battery-powered devices are also contemplated.

Examples

The following are examples of dentifrices constructed in accordance with the present invention.

Examples

TABLE I

| Trade Name or Common Name | Example #1 Wt % | Example #2 Wt % |
| --- | --- | --- |
| Sodium Fluoride, USP | 0.243 | 0.243 |
| Sorbitol, 70% Soln | 50.544 | 50.744 |
| Silica, Zeodent 109 | 12.000 | 12.000 |
| Silica, Zeodent 119 | 10.000 | 10.000 |
| Purified Water, USP | 10.000 | 10.000 |
| Sodium Acid Pyrophosphate, FCC | 4.163 | 4.163 |
| Sodium Lauryl Sulfate (28% Sol'n) | 3.500 | 3.500 |
| Sodium Hydroxide solution, FCC (50%), | 3.000 | 3.000 |
| Cocamidopropyl Betaine | 2.500 | 2.500 |
| Carbomer 956 | 1.000 | 1.000 |
| Starburst Peppermint Flavor | 0.800 | 0.800 |
| Polyethylene Specks, White | 0.750 | 0.750 |
| Xanthan Gum, NF | 0.400 | 0.400 |
| Saccharin Sodium, USP | 0.400 | 0.400 |
| Dibromofluorescein, D&C Yellow #5 | 0.400 | 0.200 |
| Exotic Orange Flavor | 0.200 | 0.200 |
| CMC Sodium, USP (7M8SF) | 0.100 | 0.100 |
| TOTALS | 100.000 | 100.000 |

Test Methods

Absorbance and Transmittance are related via the following equations.

Transmittance:

$$T = \frac{P}{P_o}$$

where T is the transmittance; P is the radiant power leaving a sample; and $P_o$ is the incident power directed at the sample.

Percent Transmittance:

$$\%T = 100 * T$$

Absorbance:

$$A = \log_{10}\left(\frac{P_o}{P}\right)$$

also $$A = \log_{10}\left(\frac{1}{T}\right)$$

also $$A = \log_{10}\left(\frac{100}{\% T}\right)$$

and $$A = 2 - \log_{10}(\% T)$$

where $P_o$, P, and T, are defined above.

Method for measuring the spectral absorbance profile and absorbance maxima(s) of an agent. Measurement of $\lambda_C$ and $\lambda_D$.

The absorbance maxima wavelength of a particular agent or mixture of agents is determined from a spectral scan of a solution of the agent(s) relative to a blank background sample. The maxima is the wavelength where the sample reaches a maximal absorbance relative to the surrounding wavelengths. A sample may have one or more maximas throughout the wavelength range of interest depending on the number and type of agent being measured. The spectral scan of a sample is obtained using a UV-VIS spectrophotometer such as an Agilant 8453 from Agilant Technologies, 395 Page Mill Rd, Palo Alto, Calif., United States. Similar instruments with the same ability to measure absorbance may also be used, however, it is necessary to use a reverse optic spectrophotometer when measuring the spectral absorbance properties of fluorescent agents to avoid interferences from fluorescence. The term reverse optic means the wavelength filter is after the sample rather than in front of the sample.

For water soluble agents, the spectral scan of the agent is obtained from an aqueous solution of the agent. The scan of the disclosing agent must be obtained using an agent concentration where the absorbance at the maxima(s) wavelengths is linearly related to the concentration of the agent in the sample solutions per Beer's law.

Beer's law states the absorbance is equal to molar absorbtivity X concentration of the agent X path length. The range of concentrations where the agent is linearly related to the concentration depends on the molar absorbtivity of the agent. Each agent has a molar absorbtivity and it may be the same, similar or drastically different from other agents. Therefore, a concentration series experiment must first be conducted to verify the linear range.

In general, the absorbance values of the sample should be greater than 0.2 and less than 1.2 for the linear range of operation. However, the linear range should be verified for each agent prior to selecting the concentration range for measuring the spectral scan to determine maxima wavelengths.

The samples are measured relative to a blank standard. A blank standard is a solution the same as the test sample except without the agent or agents. In the blank sample, the agent or agents should be replaced with the primary solvent, typically water. To make the measurements, the samples and a blank standard should be placed in a 1 cm quartz cuvet. The first step in the measurement process is to measure the blank sample as the background. Once the background sample is collected, subsequent scans of test samples may be obtained. For the purpose of this test method, the minimum scan range is from 380 nm to 800 nm to cover the visible spectrum. The scanning increments are 2 nm or less and the integration time is 0.5 seconds.

To measure the absorbance maximas of agents in composition, insoluble particulates must be removed from the composition prior to measuring. Typically, the composition can be diluted with water and centrifuged to separate the insoluble particulates. If after centrifugation, the resultant supernatants are not substantially clear, the sample is not appropriate for UV-VIS measurement due to physical interference of the light. When measuring a composition, it is important to prepare a blank standard with the same background matrix with the agent at the same dilution ratios.

If an agent is not water soluble, alternative solvents may be used as long as they do not interfere with the spectral scan measurements in the visible range. For example, alcohol may be used for some agents.

Method for measuring the fluorescence maxima of a disclosing agent(s). Measurement of $\lambda_E$.

The excitation and emission wavelengths of a particular fluorescent agent or mixture of agents are determined from fluorescence spectra plots of a solution of the agent(s) using a spectrofluorometer such as SpectraMax Gemini or SpectraMax M5 from Molecular Devices, Sunnyvale, Calif. The excitation maxima is the excitation wavelength relative to the surrounding wavelengths where the sample reaches a maximal fluorescence emission. Similarly, the emission maxima is the wavelength where the sample emits energy at a relative maximal to the surrounding emission wavelengths. A sample may have one or more excitation and emission maximas throughout the wavelength range of interest depending on the number and type of agent(s) being measured. The spectral scan of the agent is obtained from a solution of the agent. The solvent used to detect the fluorescence properties depends upon the particular agent being evaluated and the context of the intended use. Examples of typical solvents include water and methanol. The spectrofluorometer scans of the agent must be obtained using an agent concentration where the excitation and emission maxima(s) wavelengths are within the dynamic range of the instrument. The range of concentrations where the agent is within the range of the instrument depends on the quantum yield or total light output of the agent at the measured excitation wavelength. Therefore, a concentration series experiment must be conducted to verify the concentrations being used are within the dynamic range of the instrument. The instrument should be calibrated to fluorescence standards for quantitation of fluorescent agents per the manufacturer's instructions and the impact of other agents in the solvent/matrix must be included in the interpretation of the results. Measuring the fluorescence properties of agents in a composition requires the insoluble particulates to be removed from the composition prior to measuring. The composition is diluted with the measurement solvent and centrifuged to remove the particulates. If after centrifugation, the resultant supernatants are not substantially clear, the sample is not appropriate for measurement due to physical interference of the light. When measuring a composition, it is important to assess the fluorescence properties of the background matrix at the same dilution ratios.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be combined with or substituted for, in whole or part, any other feature, characteristic, component, composition, ingredient product, step or methodology described herein. Numerous alternative embodiments could be implemented, using either current technology or technology developed after the filing date of this patent, which would still fall within the scope of the claims.

What is claimed is:

1. A dentifrice composition comprising:
   a disclosing agent capable of fluorescing, thereby highlighting plaque within an oral cavity, wherein the disclosing agent is dibromofluorescein, and wherein the dentifrice composition comprises from about 0.05% to 0.1% dibromofluorescein; and wherein the dibromofluorescein does not cause staining;
   from about 0.0025% to about 5.0% of a fluoride source; and
   from about 10% to about 50% of an abrasive;
   wherein the dibromofluorescein is not readily visually perceptible under ambient light after rinsing and/or expectorating;
   wherein the dibromofluorescein fluoresces in response to electromagnetic energy having wavelengths that are within the visible spectrum;
   wherein the dibromofluorescein emits electromagnetic energy greater than 530 nm;
   wherein the dibromofluorescein is capable of fluorescing after a user rinses and/or expectorates the dentifrice composition from the oral cavity;
   wherein the dentifrice composition is suitable for home use.

2. An oral hygiene kit comprising:
   a dentifrice composition comprising:
   from about 0.05% to 0.1% of a disclosing agent capable of fluorescing, thereby highlighting plaque within an oral cavity, wherein the disclosing agent is dibromofluorescein; wherein the dibromofluorescein emits electromagnetic energy greater than 530 nm; wherein the dibromofluorescein does not cause staining; wherein the dentifrice composition is suitable for home use;

wherein the dibromofluorescein fluoresces in response to electromagnetic energy having wavelengths that are within the visible spectrum; and wherein the dibromofluorescein is not readily visually perceptible under ambient light after rinsing and/or expectorating;
from about 0.0025% to about 5.0% of a fluoride source; and
from about 10% to about 50% of an abrasive;
wherein the disclosing agent is capable of fluorescing after a user rinses or expectorates the dentifrice composition from the oral cavity;
an oral hygiene device comprising a body having a handle region and a head region, wherein an energy source is disposed in the head region, wherein the energy source is capable of providing visible light and wherein the energy applied to the disclosing agent causes the disclosing agent to fluoresce and wherein the energy source includes an LED wherein the LED has a Flux Density at a Representative Tooth Surface of from about 0.1 mW/cm$^2$ to about 20 mW/cm$^2$.

3. A method of identifying plaque within the oral cavity at home, the method comprising:
applying a dentifrice composition to the oral cavity for a period of time from about 5 seconds to about 120 seconds, wherein the dentifrice composition comprises:
from about 0.05% to 0.1% of a disclosing agent which is dibromofluorescein wherein the dibromofluorescein does not cause staining; and
from about 0.0025% to about 5.0% of a fluoride source; and
from about 10% to about 50% of an abrasive;
rinsing and/or expectorating the dentifrice composition from the oral cavity wherein the dibromofluorescein is not readily visually perceptible under ambient light after rinsing and/or expectorating; wherein the dibromofluorescein fluoresces in response to electromagnetic energy having wavelengths that are within the visible spectrum; and wherein the dibromofluorescein emits electromagnetic energy greater than 530 nm;
applying energy from an energy source to the oral cavity wherein the energy source is capable of providing visible light and wherein the energy source includes an LED wherein the LED has a Flux Density at a Representative Tooth Surface of from about 0.1 mW/cm$^2$ to about 20 mW/cm$^2$;
viewing the plaque within the oral cavity; and
performing a cleaning operation to reduce the presence of the plaque.

4. The method of claim 3 wherein the dentifrice composition is applied to the oral cavity by an oral hygiene device comprising:
a body having a handle region and a head region; and
a plurality of bristles disposed in the head region, at least a portion of the plurality of bristles defining a substantially orange color.

5. The method of claim 4 wherein the head region comprises the energy source.

6. The method of claim 3 further comprising the step of applying a mouthrinse comprising the disclosing agent.

7. The dentifrice composition of claim 1 wherein the composition comprises greater than about 0.07% and less than about 0.08% dibromofluorescein.

8. The dentifrice composition of claim 1 further comprising an opacifying agent selected from the group consisting of titanium dioxide, mica, mica coated titanium dioxide, polypropylene, polyester particulates, and combinations thereof.

9. The dentifrice composition of claim 8 wherein the opacifying agent comprises titanium dioxide.

10. The dentifrice composition of claim 1 wherein at least a portion of the dentifrice composition is opaque.

11. The oral hygiene kit of claim 2 wherein the dentifrice composition comprises greater than about 0.07% and less than about 0.08% dibromofluorescein.

12. The oral hygiene kit of claim 2 wherein the dentifrice composition further comprises an opacifying agent selected from the group consisting of titanium dioxide, mica, mica coated titanium dioxide, polypropylene, polyester particulates, and combinations thereof.

13. The oral hygiene kit of claim 12 wherein the opacifying agent comprises titanium dioxide.

14. The method of claim 3 wherein the dentifrice composition comprises greater than about 0.07% and less than about 0.08% dibromofluorescein.

15. The method of claim 3 wherein the dentifrice composition further comprises an opacifying agent selected from the group consisting of titanium dioxide, mica, mica coated titanium dioxide, polypropylene, polyester particulates, and combinations thereof.

16. The method of claim 15 wherein the opacifying agent comprises titanium dioxide.

17. The method of claim 3 wherein at least a portion of the dentifrice composition is opaque.

* * * * *